(12) United States Patent
Liu et al.

(10) Patent No.: US 8,961,578 B2
(45) Date of Patent: Feb. 24, 2015

(54) DERMATOLOGICAL TREATMENT DEVICE WITH ONE OR MORE VERTICAL CAVITY SURFACE EMITTING LASERS (VCSEL)

(71) Applicant: Tria Beauty, Inc., Dublin, CA (US)

(72) Inventors: Harvey I-Heng Liu, Fremont, CA (US); Tobin C. Island, Oakland, CA (US); Patrick Reichert, Dublin, CA (US)

(73) Assignee: Tria Beauty, Inc., Dublin, CA (US)

( * ) Notice: Subject to any disclaimer, the term of this patent is extended or adjusted under 35 U.S.C. 154(b) by 0 days.

(21) Appl. No.: 13/848,460

(22) Filed: Mar. 21, 2013

(65) Prior Publication Data

US 2013/0253487 A1 Sep. 26, 2013

Related U.S. Application Data

(60) Provisional application No. 61/613,778, filed on Mar. 21, 2012.

(51) Int. Cl.
| | |
|---|---|
| *A61N 5/06* | (2006.01) |
| *A61B 18/18* | (2006.01) |
| *A61B 18/20* | (2006.01) |
| *H01S 5/42* | (2006.01) |
| *A61B 18/00* | (2006.01) |

(52) U.S. Cl.
CPC ............. *A61B 18/203* (2013.01); *H01S 5/423* (2013.01); *A61N 5/0616* (2013.01); *A61B 2018/0016* (2013.01); *A61B 2018/00452* (2013.01); *A61B 2018/208* (2013.01)
USPC .................................. 607/88; 607/89; 606/9

(58) Field of Classification Search
CPC . A61N 2005/067; A61N 5/062; A61B 18/203
USPC ............................................. 607/88, 89; 606/9
See application file for complete search history.

(56) References Cited

U.S. PATENT DOCUMENTS

| | | | |
|---|---|---|---|
| 6,959,027 B1 | 10/2005 | Guilfoyle et al. | 372/50.1 |
| 7,118,563 B2 | 10/2006 | Weckwerth et al. | 606/9 |

(Continued)

FOREIGN PATENT DOCUMENTS

| | | | |
|---|---|---|---|
| WO | 2011/010239 A1 | 1/2011 | A61B 18/20 |
| WO | 2011/021140 A2 | 2/2011 | B23K 26/06 |
| WO | 2012/106678 A1 | 8/2012 | A61B 18/20 |

OTHER PUBLICATIONS

International Search Report and Written Opinion, Application No. PCT/US2013/033338, 13 pages, Jul. 3, 2013.

(Continued)

*Primary Examiner* — Lynsey Crandall
*Assistant Examiner* — Sebastian X Lukjan
(74) *Attorney, Agent, or Firm* — King & Spalding L.L.P.

(57) ABSTRACT

A device for providing laser-based dermatological treatments may include a device body having an application end, a VCSEL laser supported in the device body and including multiple emitter zones, each emitter zone comprising one or more micro-emitters, each micro-emitter configured to emit a micro-beam, wherein at least two of the multiple emitter zones are configured such that the micro-beam emitted by the micro-emitters of the at least two emitter zones form a combined beam through the application end of the device to provide a treatment spot on the skin, and electronics coupled to the at least two emitter zones and configured to control the at least two emitter zones independently.

29 Claims, 9 Drawing Sheets

(56) References Cited

U.S. PATENT DOCUMENTS

| | | | |
|---|---|---|---|
| 7,250,045 B2 | 7/2007 | Island et al. | 606/17 |
| 7,413,567 B2 | 8/2008 | Weckwerth et al. | 606/10 |
| 7,452,356 B2 | 11/2008 | Grove et al. | 606/9 |
| 7,981,111 B2 | 7/2011 | Grove et al. | 606/27 |
| 8,512,322 B1 | 8/2013 | Liu et al. | 606/9 |
| 2006/0009749 A1 | 1/2006 | Weckwerth et al. | 606/9 |
| 2007/0032847 A1 | 2/2007 | Weckwerth et al. | 607/93 |
| 2008/0027518 A1 | 1/2008 | Island et al. | 607/88 |
| 2008/0172047 A1* | 7/2008 | Altshuler et al. | 606/9 |
| 2008/0310836 A1 | 12/2008 | Weckwerth et al. | 398/9 |
| 2009/0097513 A1 | 4/2009 | Grove et al. | 372/25 |
| 2009/0125006 A1 | 5/2009 | Weckwerth et al. | 606/9 |
| 2009/0204109 A1 | 8/2009 | Grove et al. | 606/9 |
| 2009/0270848 A1 | 10/2009 | Weckwerth et al. | 606/9 |
| 2010/0069898 A1 | 3/2010 | O'Neil et al. | 606/9 |
| 2010/0196343 A1 | 8/2010 | O'Neil et al. | 424/94.4 |
| 2011/0098789 A1 | 4/2011 | Weckwerth et al. | 607/88 |
| 2012/0226268 A1 | 9/2012 | Liu et al. | 606/9 |
| 2012/0232536 A1 | 9/2012 | Liu et al. | 606/9 |
| 2012/0232537 A1 | 9/2012 | Liu et al. | 606/9 |
| 2012/0232538 A1 | 9/2012 | Liu et al. | 606/9 |
| 2012/0232539 A1 | 9/2012 | Liu et al. | 606/9 |
| 2012/0239016 A1 | 9/2012 | Liu et al. | 606/9 |

OTHER PUBLICATIONS

Liu, Anjin et al., "Reduced Divergence Angle of Photonic Crystal Vertical-Cavity Surface-Emitting Laser," Appl. Phys. Lett. 94, 3 pages, 2009.

Kang, Zhou et al., "Reduction of Far-Field Divergence Angle of 850 nm Multi-Leaf Holey Vertical Cavity Surface Emitting Laser," Chin. Phys. Lett., vol. 28, No. 8, 3 pages, 2011.

* cited by examiner

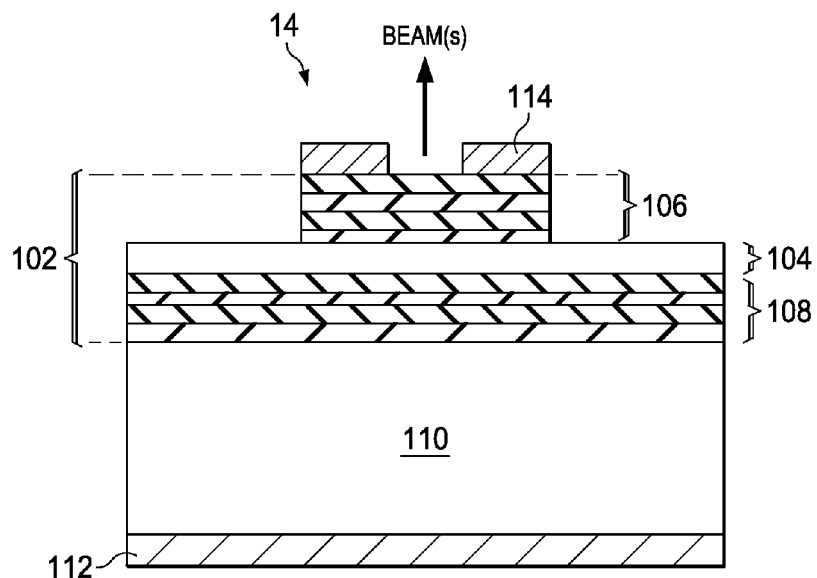
FIG. 2
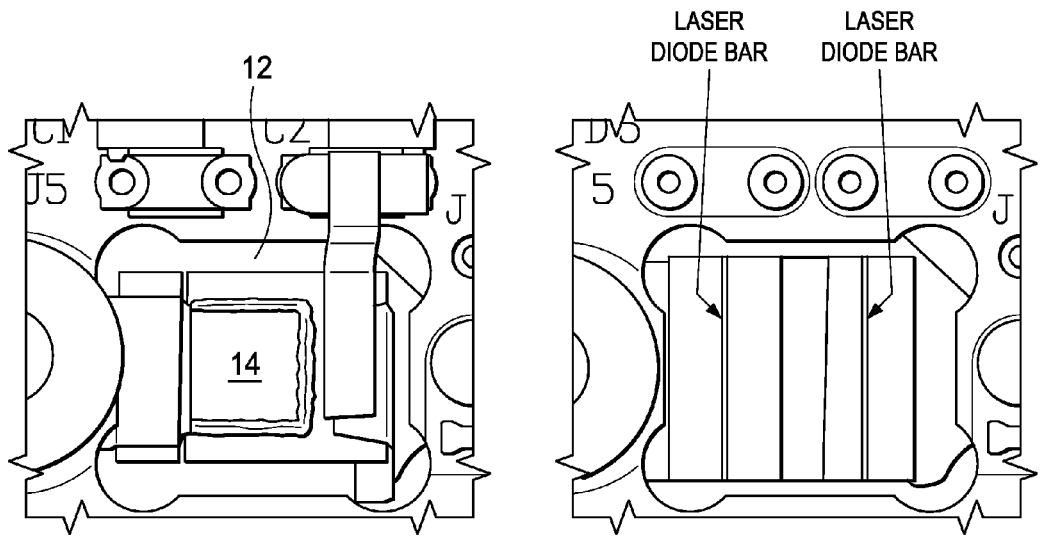
FIG. 3A
FIG. 3B
(PRIOR ART)

DERMATOLOGICAL TREATMENT DEVICE WITH ONE OR MORE VERTICAL CAVITY SURFACE EMITTING LASERS (VCSEL)

CROSS-REFERENCE TO RELATED APPLICATIONS

This application claims the benefit of U.S. Provisional Application No. 61/613,778 filed on Mar. 21, 2012, which disclosure is herein incorporated by reference in its entirety.

TECHNICAL FIELD

The present disclosure is related to dermatological treatment devices that include one or more Vertical Cavity Surface Emitting Lasers (VCSEL).

BACKGROUND

Laser-based treatment of tissue is used for a variety of applications, such as hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. Such treatments generally include delivering laser radiation to an area of tissue on a person's body, e.g., the skin or internal tissue, to treat the tissue in a photochemical, photobiological, thermal, or other manner, which can be ablative or non-ablative, among other properties, depending on the particular application.

Laser-based treatment devices may include any suitable type of laser, e.g., laser diode, fiber laser, LED, etc. A device may include a single laser or multiple lasers, e.g., a laser diode bar including multiple distinct emitters arranged in a row, or multiple fiber lasers arranged in a row or array.

Edge-emitting diode lasers are commonly used for certain treatments and devices for providing such treatments. Edge-emitting diode lasers emit a beam having an axis-asymmetric profile in a plane transverse to the optical axis of the laser. In particular, the emitted beam diverges significantly faster in a first axis (referred to as the "fast axis") than in an orthogonal second axis (referred to as the "slow axis"). In contrast, other types of lasers, e.g., fiber lasers, typically emit a beam having an axis-symmetric profile in the transverse plane.

Laser-baser treatment devices include larger-scale devices typically operated by a physician or other professional in a clinic or other office, as well as hand-held devices for home-use, allowing users to provide treatment to themselves. Some hand-held laser-baser treatment devices are battery powered, e.g., using a Li ion battery cell (or multiple cells). Such battery-powered devices may be recharged between use, e.g., by plugging into an A/C wall outlet, either directly or by docking in a docking unit plugged into the wall.

Some laser-baser treatment devices apply laser radiation directly from the laser source to the target tissue to create a pattern of radiated areas (e.g., spots, lines, or other shapes) in the tissue. Others include optics between the laser source and the target tissue. Such optics may include optical elements such as lenses, mirrors, and other reflective and/or transmissive elements, for controlling optical parameters of the beam, such as the direction, shape (e.g., convergent, divergent, collimated), spot size, angular distribution, temporal and spatial coherence, and/or intensity profile of the beam. Some devices include systems for scanning a laser beam in order to create a pattern of radiated areas (e.g., spots, lines, or other shapes) in the tissue. For some applications, the scanned pattern of radiated areas overlap each other, or substantially abut each other, or are continuous, in order to provide generally complete coverage of a target area of tissue. For other applications, e.g., certain wrinkle treatments and other skin rejuvenation treatments, the scanned radiated areas may be spaced apart from each other such that only a fraction of the overall target area of the tissue is radiated. In this case, there are generally regions of untreated tissue between regions of treated tissue. This latter type of treatment is known as "fractional" treatment (or more specifically, fractional photothermolysis) because only a fraction of the target area is irradiated.

Laser-baser treatment devices may deliver radiation as continuous wave (CW) radiation, manually pulsed radiation, automatically pulsed radiation, or in any other manner, and according to any suitable parameters, e.g., wavelength, current, power level, etc. For example, a wavelength of about 650 nm to about 1100 nm (e.g., about 810 in some applications) may be used for hair removal treatment. As another example, wavelengths absorbed by water in the skin, e.g., between 1400 nm and 2000 nm, may be used for certain treatments. For certain "fractional" skin treatments, a wavelength of about 1450-1550 nm±50 nm may be used, with a total energy of about 2 mJ-30 mJ delivered to the target tissue at each treatment zone, or "microthermal zone" (MTZ).

SUMMARY

Embodiments of the present disclosure provide methods and device for using VCSEL (vertical-cavity surface-emitting laser) lasers in dermatological treatment devices. VCSEL chips provide radiation over a range of wavelengths, e.g., 640 nm to 1300 nm (e.g., VCSEL chips based on gallium arsenide (GaAs) wafers with distributed Bragg reflectors (DBRs) formed from GaAs and aluminum gallium arsenide (AlxGa(1-x)As)), and 1300 nm to 2000 nm (e.g., VCSEL chips using indium phosphide for at least the active region). VCSEL lasers (e.g., high-power VCSELs) may be used as the radiation source for various types of dermatological treatment applications, including for example, large area treatments and/or fractional treatments.

In some embodiments, devices include one or more high-power VCSEL 2-D surface-emitting laser to provide dermatological treatments. Such devices may provide a number of advantages as compared to existing edge-emitting laser diodes and laser diode bars used in most laser-based dermatological devices. For example, using VCSELs allows for engineering and control of the treatment beam profile, where the treatment area is defined directly by the laser source.

Some embodiments utilize VCSEL(s) to provide large area treatments. Other embodiments utilize VCSEL(s) to create spatially separated independently addressable laser emitter zones on a single VCSEL chip, e.g., to enable various 2-D all-solid-state fractional treatment devices, or other dermatological devices where energy zones are useful or desired. These 2-D laser arrays can concurrently generate multiple spaced-apart "micro thermal zones," or MTZs, without any moving scanner and may achieve high treatment coverage rates.

In some aspects or embodiments of the present disclosure, a dermatological treatment device includes a device body having an application end, a VCSEL laser supported in the device body, the VCSEL laser including multiple emitter zones, each emitter zone comprising one or more micro-emitters, each micro-emitter configured to emit a micro-beam, wherein at least two of the multiple emitter zones are configured such that the micro-beam emitted by the micro-emitters of the at least two emitter zones form a combined beam through the application end of the device to provide a treatment spot on the skin, and electronics coupled to the at least two emitter zones and configured to control the at least two emitter zones independently.

In other aspects or embodiments of the present disclosure, a method for providing a laser-based dermatological treatment may include providing a device having a VCSEL laser supported in a device body, the VCSEL laser including multiple emitter zones, each emitter zone comprising one or more micro-emitters, each micro-emitter configured to emit a micro-beam, wherein at least two of the multiple emitter zones are configured such that the micro-beam emitted by the micro-emitters of the at least two emitter zones form a combined beam through the application end of the device to provide a treatment spot on the skin; and using electronics coupled to the at least two emitter zones to control the at least two emitter zones independently.

In other aspects or embodiments of the present disclosure, a VCSEL laser for use in a device for providing radiation-based dermatological treatments, the device comprising an array of micro-emitters arranged on a chip, each configured to emit a micro-beam, wherein the array of micro-emitters is divided into multiple emitter zones, each emitter zone comprising one or more micro-emitters, and wherein at least two of the multiple emitter zones are configured to be independently addressable by associated control electronics.

BRIEF DESCRIPTION OF THE DRAWINGS

Some embodiments of the disclosure may be understood by referring, in part, to the following description and the accompanying drawings wherein:

FIG. 2 illustrates a side cross-sectional view of an example VCSEL chip, according to certain embodiments;

FIG. 3A shows an example square-shaped VCSEL chip mounted on a treatment device, according to an example embodiment;

FIG. 3B shows a pair of edge-emitting laser diode bars mounted on a conventional treatment device;

DETAILED DESCRIPTION OF THE DRAWINGS

Figure 1:
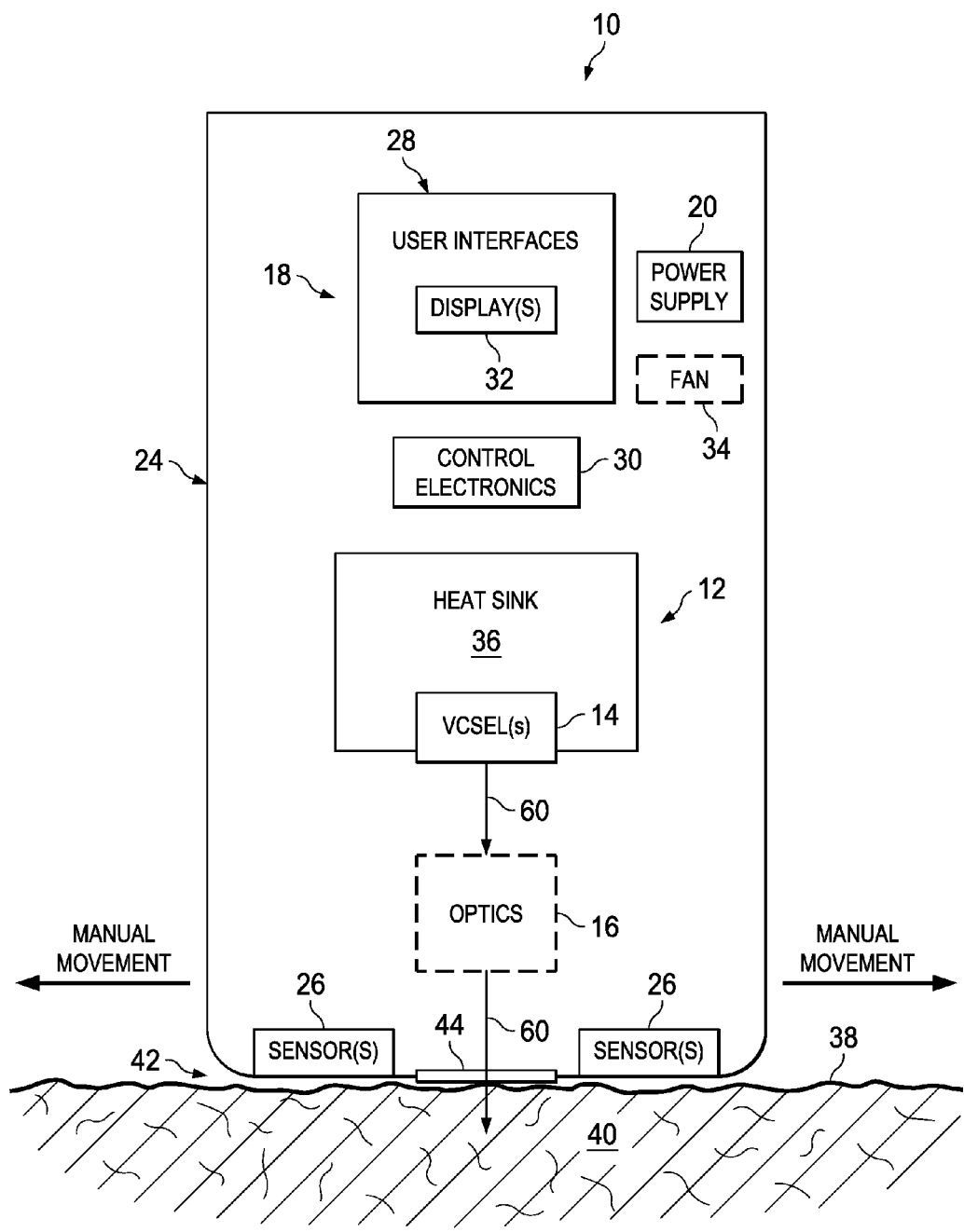
FIG. 1 illustrates components of an example dermatological treatment device including one or more Vertical Cavity Surface Emitting Laser (VCSEL) as a radiation source, according to certain embodiments.

In some embodiments, a hand-held compact device includes one or more Vertical Cavity Surface Emitting Lasers (VCSEL) for providing laser-based dermatological treatments, e.g., skin resurfacing, skin rejuvenation, wrinkle treatment, removal or reduction of pigmentation, hair removal, acne treatment, skin tightening, redness, vascular treatments such as telangectasia or port-wine stains, stretch marks, anti-aging, or anti-inflammatory skin treatments such as treating rosacea, acne, or vitiligo. Other embodiments may apply to non-skin tissue treatment, such as eye tissue or internal organs.

In some example embodiments, the device is a compact-hand-held device for providing laser-based hair removal by providing pulsed or continuous wave ("CW") radiation as the device is moved across the skin, e.g., in a gliding mode or a stamping mode. In other example embodiments, the device is a compact-hand-held device for providing laser-based non-ablative fractional treatment by pulsing one or more VCSELs as the device is moved across the skin.

The device may include one or more VCSELs that deliver one or more laser beams to the skin to produce one or more irradiated areas on the skin that provide a dermatological treatment. The VCSEL(s) may be operated to provide one or more beams in any suitable manner, such as pulsed, continuous wave (CW), or otherwise, depending on the particular embodiment, application, or device setting.

A VCSEL may be configured to generate a single beam or multiple discrete beams to the skin. For the latter, the VCSEL may include non-active regions that define an array of emitter zones separated from each other by non-active (or less active or masked) regions, with each emitter zone generating a beam. Thus, a single VCSEL may generate and deliver an array (e.g., a 1D or 2D array) of multiple discrete beams to the skin concurrently, successively, or according to any other timing protocol), to create an array of spaced-apart treatment spots on the skin, e.g., to provide a fractional treatment via a manual gliding mode or stamping mode operation of the device.

In some embodiments, the beam generated from each emitter zone is substantially axially-symmetric (e.g., as opposed to the beam generated by an edge emitting laser diode). In some embodiments, a two-dimensional multi-zone pulsed VCSEL may be configured in direct exposure, close proximity (in effect, placed directly or nearly directly against the skin) to affect a fractional treatment when glided or stamped across the skin. Likewise, a one-dimensional, multi-zone pulsed VCSEL can be configured in direct exposure, close proximity to affect a fractional treatment when glided or stamped across the skin.

As discussed above, in some embodiments, the device provides pulsed energy beams to the skin to provide a fractional dermatological treatment, e.g., skin resurfacing, skin rejuvenation, wrinkle treatment, removal or reduction of pigmentation, treatment of coarse skin caused by photodamage, etc. Each pulsed energy beam forms an irradiated treatment spot (or "treatment spot") on the surface of the skin, and a three-dimensional volume of thermally damaged (or otherwise influenced, such as photochemically) skin extending below the surface of the skin, referred to herein as a micro thermal zone (MTZ). Each MTZ may extend from the skin surface downward into the skin, or may begin at some depth below the skin surface and extend further downward into the skin, depending on the embodiment, device settings, or particular application. The device may be configured to generate an array of MTZs in the skin that are laterally spaced apart from each other by volumes of untreated (i.e., non-irradiated or less irradiated) skin. For example, an application end of the device (also referred to herein as the device "tip") may be manually moved (e.g., in a sliding manner) across the surface of the skin during a treatment session. An energy beam or beams may be pulsed (to generate MTZs in the skin) during the movement of the device across the skin (referred to herein as a "gliding mode" treatment), or between movements of the device to different locations on the skin (referred to herein as a "stamping mode" treatment), or a combination of these modes or different modes. The skin's healing response, promoted by the areas of untreated (i.e., non-irradiated) skin between adjacent MTZs, provides fractional treatment benefits in the treatment area (e.g., skin resurfacing or rejuvenation, wrinkle removal or reduction, pigment removal or reduction, etc.). In some embodiments or applications, the compact, hand-held device may yield results similar to professional devices, but leverages a home use model to more gradually deliver the equivalent of a single professional dose over multiple treatments or days. Skin rejuvenation generally includes at least one or more of treatments for wrinkles, dyschromia, pigmented lesions, actinic kerotosis, melasma, skin texture, redness or erythema, skin tightening, skin laxity, and other treatments.

As used herein, "fractional" treatment means treatment in which individual treatment spots generated on the skin surface are physically separated from each other by areas of non-irradiated (or less irradiated) skin (such that the MTZs corresponding to such treatment spots are generally physically separated from each other). In other words, in a fractional treatment, adjacent treatment spots (and thus their corresponding MTZs) do not touch or overlap each other. In some embodiments in which one or more VCSELs are pulsed to generate a successive series of treatment spots on the skin, the pulse rate may be set or selected based on a typical or expected speed at which the device is manually moved or "glided" across the skin, referred to herein as the "manual glide speed" (e.g., in a gliding mode operation of the device). In particular, the pulse rate may be set or selected such that for a range of typical or expected manual (or mechanically-driven) glide speeds, adjacent treatment spots are generally physically separated from each other by areas of non-treated skin (i.e., fractional treatment is provided). In some embodiments, the pulse rate may be set or selected such that for a range of typical or expected manual glide speeds, adjacent treatment spots are physically separated from each other from a predetermined minimum non-zero distance, e.g., 500 μm. For example, in some embodiment, a pulse rate of between 2 and 30 HZ (e.g., about 15 Hz) may be selected for providing a desired fractional treatment for typical or expected manual glide speeds of between 1 and 6 cm/sec.

In some embodiments, the device may be controlled to prevent, limit, or reduce the incidence or likelihood of treatment spot overlap, e.g., based on feedback from one or more sensors (e.g., one or more dwell sensors, motion/speed sensors, and/or displacement sensors). For example, the device may monitor the speed or displacement of the device relative to the skin and control the VCSEL(s) accordingly, e.g., by turning off the VCSEL(s), reducing the pulse rate, etc. upon detecting that the device has not been displaced on the skin a minimum threshold distance from a prior treatment location. Further, in some embodiments, the pulse rate may be automatically adjustable by the device and/or manually adjustable by the user, e.g., to accommodate different manual glide speeds and/or different comfort levels or pain tolerance levels of the user.

In some embodiments, the device is configured to be manually scanned across the skin, rather than using an automated scanning system (e.g., including systems for moving optical elements and/or the laser or other energy source) present in various existing devices. In some embodiments the device does not include any moving optics (or any optics at all, as discussed below). In some embodiments, both the VCSEL(s) and beam path(s) from the VCSEL(s) to the skin are fixed with respect to the device housing.

Further, the device may be configured for "direct exposure" or "indirect exposure" radiation, and/or for "close proximity" or "remote proximity" radiation, depending on the particular embodiment and/or configuration of the device. "Direct exposure" embodiments or configurations do not include any optics downstream of the VCSEL(s) for affecting or treating the beam(s) generated by the VCSEL(s) (the term "optics" is defined below in this document). Some direct exposure devices may include a window (e.g., to protect the VCSEL(s) and/or other internal components of the device) that does not substantially affect the beam. A window may be formed from any suitable material, e.g., sapphire, quartz, diamond, or other material transparent at the frequency of the VCSEL(s) 14 and may also have a good thermal coefficient.

Thus, embodiments of the device may create a desired pattern of MTZs without using microlenses or other similar optics. Thus, embodiments of the device may provide increased optical efficiency, reduced power requirements, simpler and less expensive manufacturing, increased compactness, and/or enhanced reliability as compared with certain non-ablative fractional treatment devices that use microlenses or other similar optics for creating MTZ arrays. However, it should be understood that certain embodiments of the device may include one or more optics, e.g., for desired beam shaping.

The omission of beam-influencing optics in certain embodiments may result in an overall higher optical efficiency for the device. In any optical system, losses occur due to less than perfect transmission, reflection, or beam "spilling" outside of the diameter of the optical element(s) in the beam path. Thus, embodiments of the device that omit beam-influencing optics may provide increased optical efficiency, and thus allow reduced power to the VCSEL(s), as compared with certain conventional devices.

In contrast, "indirect exposure" embodiments or configurations include one or more optics downstream of the VCSEL(s) for affecting or treating the beam(s) generated by the VCSEL(s). Optics may allow the VCSEL(s) to be positioned at any desired distance from the application end of the device that contacts the skin during treatment (and thus at any desired distance from the target surface) or to affect other radiation properties. As discussed below, certain embodiments that incorporate a multi-beam VCSEL may include beam spacing elements to provide a desired spacing between treatment spots on the skin.

In "close proximity" embodiments or configurations, the emitting surface of the VCSEL is positioned within 10 mm of the skin-contacting surface of the device (i.e., the leading surface of the device tip), such that the emitting surface of the VCSEL is positioned within 10 mm of the skin surface when the device tip is positioned in contact with the skin. As discussed below, this distance is referred to herein as the "proximity gap spacing." In contrast, in "remote proximity" embodiments or configurations, the proximity gap spacing (between the emitting surface of the VCSEL and the skin-contacting surface of the device) is greater than 10 mm. Some close proximity embodiments, due to the small proximity gap spacing and thus short travel distance of the beam(s) from the VCSEL to the skin, may omit precision-aligned optics (or all optics) that may be needed in similar remote proximity embodiments, thus providing a direct exposure, close proximity configuration. Some particular embodiments discussed below include a VCSEL source configured for direct exposure and close proximity radiation, wherein the emitting surface of the VCSEL is positioned within 10 mm of the skin surface, with no optics (e.g., only a window, open space, protective coating, or similar feature) between the VCSEL and the skin. Direct exposure, close proximity embodiments may be particularly compact. Some direct exposure, close proximity embodiments may provide a high optical throughput and may be capable of generating relatively high-power emissions in a compact battery-operated device.

It should be understood that "direct exposure" is not synonymous with "close proximity," and likewise "indirect exposure" is not synonymous with "remote proximity." That is, direct exposure embodiments or configurations may be configured for either close proximity or remote proximity radiation, depending on the particular embodiment or configuration. Similarly, indirect exposure embodiments or configurations may be configured for either close proximity or remote proximity radiation, depending on the particular embodiment or configuration. For example, some embodiments may include a very small lens (e.g., a cylindrical or ball lens) downstream of the light source, but wherein the emitting surface of each VCSEL is still within 10 mm of the skin surface during treatment.

In some embodiments, the VCSEL engine and delivery components (if any) of the device have an all-solid-state construction that excludes any automated or mechanically moving parts for dynamically moving the VCSEL or the direction or location of the propagated beam(s) relative to the device housing, e.g., including (a) any motorized or otherwise moving beam-scanning elements, such as motorized or otherwise moving optical elements to scan a beam to multiple different directions or locations relative to the device housing (e.g., galvo-controlled mirrors or rotating multi-faceted scanning elements), and (b) any motorized or other elements for physically moving the VCSEL and any associated beam delivery elements (e.g., a laser, LED, fiber, waveguide, etc.). Such embodiments may reduces noise, increase the reliability of the device, reduce manufacturing cost and complexity, and/or increase compactness of the finished device with low or minimal component count.

In some embodiments, the device has an all-solid-state construction with no automated moving parts at all, including no any automated or mechanically moving parts for dynamically moving the VCSEL and direction and location of the propagated laser beam(s) relative to the device housing (as discussed above), as well as any fans, other motors, or other automated moving parts.

Certain example embodiments are handheld, battery powered, compact skin treatment devices with all solid-state components, configured to provide direct exposure and/or close-proximity radiation using one or more VCSEL chips, and for providing skin area coverage via manual scanning of the device across the surface of the skin, in a gliding or stamping mode operation, and using one or more CW or pulsed VCSELs.

In some embodiments, the device is fully or substantially self-contained in a compact, hand-held housing. For example, in some battery-powered embodiments of the device, the VCSEL(s), user interface(s), control electronics, sensor(s), battery or batteries, fan(s) or other cooling system (if any), and/or any optics (if any), are all contained in a compact, hand-held housing. Similarly, in some wall-outlet-powered embodiments of the device, the VCSEL(s), user interface(s), control electronics, sensor(s), battery or batteries, fan(s) or other cooling system (if any), and/or any optics (if any), are all contained in a compact, hand-held housing, with only the power cord extending from the device.

In other embodiments, one or more main components of the device may be separate from the device housing, and connected by any suitable physical or wireless means (e.g., wire, cable, fiber, wireless communications link, etc.)

In some embodiments, the device provides eye safe radiation, e.g., due to the divergence of the beam(s) delivered by the VCSEL(s) and/or using particular optics (e.g., a mixer and/or diffuser) and/or using an eye safety control system including one or more sensors, and/or by any other suitable manner. In some laser-based embodiments or settings, the device meets the Class 1M or better (such as Class 1) eye safety classification per the IEC 60825-1. In other laser-based embodiments or settings, the device falls outside the IEC 60825-1 Class 1M eye safety classification by less than 25% of the difference to the next classification threshold. In still other laser-based embodiments or settings, the device falls outside the IEC 60825-1 Class 1M eye safety classification by less than 50% of the difference to the next classification threshold.

In some embodiments, the device is eye safe, hand held, manufacturable without excessive labor costs, requires low power consumption, and effective. In some embodiments, the device eliminates the need for optical scanners, microlenses, or other complex optical and mechanical devices, for creating multiple MTZs in the skin. In particular embodiments, the device is battery powered, with a single, fixed location, repetitively-pulsed edge emitting laser diode for creating an array of MTZs in the skin by manually scanning the device across the skin while the VCSEL is repetitively pulsed, with each pulse creating either a single MTZ or multiple MTZs in the skin, depending on the configuration of the VCSEL chip.

FIG. 1 illustrates components of an example treatment device 10, according to certain embodiments. Treatment device 10 may include a laser engine 12 including one or more VCSELs 14 configured to generate laser radiation, in the form or one or more laser beams 60, optics 16 for delivering the laser radiation to a target area 40 (e.g., an area of tissue), a control system 18, one or more power supplies 20, and one or more fans 34.

As discussed below, "direct exposure" embodiments may omit optics 16 such that no optics are provided between VCSEL(s) 14 and the target surface, for direct exposure of the target tissue. In some direct exposure embodiments, VCSEL(s) are located in close proximity to the target skin surface (e.g., less than 10 mm, less than 2 mm, or even less than 1 mm from the target skin surface).

The components of device 10 may be provided in a structure or housing 24, or alternatively may be provided in separate structures or housings and connected in any suitable manner, e.g., via fiber optic or other cabling. Housing 24 may define an application end (or "treatment tip") 42 configured to be placed in contact with the target surface (e.g., skin) during treatment of the target area 40. Application end 42 may include or house various user interfaces, including the treatment delivery interface for delivering laser radiation to the user, as well as one or more sensors 26 for detecting various characteristics of the target surface and/or treatment delivered by device 10. In some embodiments, application end 42 may include an aperture or window 44 through which the laser radiation, in the form or one or more laser beams 60, is delivered to the target surface, or alternatively, an optical element 16 (e.g., a lens) may be located at application end 42 and configured for direct contact or very close proximity with the skin during treatment.

Device 10 may include any other components suitable for providing any of the functionality discussed herein or other related functionality known to one of ordinary skill in the art.

As discussed above, laser engine 12 may include one or more VCSELs 14. As used herein, a VCSEL refers to a VCSEL chip, which may be configured to deliver one or multiple laser beams, as discussed below. Where device 10 includes multiple VCSELs 14, the multiple VCSELs 14 may be arranged proximate each other and/or connected to each other, or may be spaced apart from each other in any suitable arrangement.

The VCSEL(s) 14 of device 10 may be configured for and/or operated at any suitable wavelength to provide the desired treatment. For example, VCSEL(s) 14 may be configured for and/or operated at a wavelength of about 810 nm (e.g., 810 nm±30 nm) for providing hair removal treatment. As used herein, the term "hair removal" encompasses both removal of hair and inhibition of hair growth/regrowth. As another example, VCSEL(s) 14 may be configured for and/or operated at a wavelength that is absorbed by water in the skin, e.g., between 1400 nm and 2000 nm, e.g., for certain photothermolysis treatments. In some embodiments, VCSEL(s) 14 may be configured for and/or operated at a wavelength of between 1400 nm and 1550 nm, e.g., for acne treatment or certain fractional non-ablative skin treatments. In other embodiments, VCSEL(s) 14 may be configured for and/or operated at a wavelength of between 1700 nm and 1800 nm, e.g., for sebaceous gland related treatment like acne. In still other embodiments, VCSEL(s) 14 may be configured for and/or operated at a wavelength of between 1900 nm and 1950 nm, e.g., for pigmented lesion treatment like solar lentigo.

Further, VCSEL(s) 14 may be configured or operated to deliver continuous wave (CW) radiation, pulsed radiation, or in any other manner. In some embodiments, device 10 controls VCSEL(s) 14 to provide CW radiation, e.g., for using device 10 in a gliding mode to provide bulk heating skin tightening, hair removal, or acne treatment. In other embodiments, device 10 controls VCSEL(s) 14 to provide manually pulsed radiation, e.g., for using device 10 in a stamping mode to provide hair removal. In still other embodiments, device 10 controls VCSEL(s) 14 to provide automatically pulsed radiation, e.g., for using device 10 in a gliding mode to provide selective photothermalysis. For example, in some embodiments, device 10 may be configured to sequentially deliver a series of laser beams to the target area 40, while being manipulated by the user in a stamping mode or in a gliding mode, to generate treatment zones (e.g., continuous or discontinuous line segments) that are spaced apart from each other by areas of non-irradiated skin between the adjacent treatment zones, to provide a fractional treatment to the tissue, e.g., for skin rejuvenation, wrinkle treatment, or treatment of pigmented legions (e.g., age spots, sun spots, moles, etc.).

Certain embodiments of device 10 include one or more optics 16 downstream of VCSEL(s) 14 for directing or treating the laser radiation emitted from VCSEL(s) 14 before reaching the target surface. Optics 16 may allow for VCSEL(s) 14 to be positioned at any desired distance from the application end 42 of the device that contacts the skin during treatment (and thus at any desired distance from the target surface). Embodiments of device 10 that include optics 16 downstream of laser engine 12 are referred to herein as "indirect exposure" embodiments.

Optics 16 may include any number and types of optical elements, e.g., lenses, mirrors, and other reflective and/or fully or partially transmissive elements, for delivering the radiation generated by laser engine 12, in the form of one or more laser beams, to the target area 40 and, if desired, for treating the one or more laser beams, such as adjusting the treatment zone size, intensity, treatment zone location, angular distribution, coherence, etc.

As used herein, an "optic" or "optical element" may mean any element that deflects a laser beam, influences the angular distribution profile (e.g., angle of convergence, divergence, or collimation) of a laser beam in at least one axis, influences the focus of the beam in at least one axis, or otherwise affects a property of the radiation. Thus, optics include mirrors and other reflective surfaces, lenses, prisms, light guides, gratings, filters, etc. For the purposes of this disclosure, optics do not generally include planar or substantially planar transmissive elements such as transmissive windows or films, such as those that serve as transmissive aperture that protect internal components.

Other embodiments of device 10 do not include any optics 16 downstream of VCSEL(s) 14. Such embodiments are referred to herein as "direct exposure" embodiments. A "direct exposure" embodiment or configuration does not include any optics downstream of the VCSEL(s) 14 for affecting or treating the beam(s) generated by VCSEL(s) 14. Some direct exposure devices may include a window (e.g., to protect the VCSEL(s) and/or other internal components of the device) that does not substantially affect the beam(s). A window may be formed from any suitable material, e.g., sapphire, quartz, diamond, or other material transparent at the frequency of the VCSEL(s) 14 and preferably also having a good thermal coefficient.

In some embodiments, VCSEL(s) 14 may be positioned very close to the application end 42 of the device that contacts the skin during treatment (and thus very close to the target surface). For example, some direct exposure devices are also configured for "close proximity" radiation, in which the VCSEL(s) 14 are positioned such that the emitting surface is less than 10 mm from the leading surface of the application end 42 (and thus less than 10 mm from the target surface when the application end 42 is placed in contact with the skin). In some embodiments, the VCSEL(s) 14 are positioned such that the emitting surface is less than 2 mm from the leading surface of the application end 42/less than 2 mm from the target surface. In particular embodiments, the VCSEL(s) 14 are positioned such that the emitting surface is less than 1 mm from the leading surface of the application end 42/less than 1 mm from the target surface. Still further, in some embodiments, the VCSEL(s) 14 are positioned such that the emitting surface is less than 500 µm, 200 µm, or even 100 µm from the leading surface of the application end 42 or the target surface.

Control system 18 may be configured to control one or more components of device 10 (e.g., laser engine 12 and/or a beam scanning system 142). Control system 18 may include, for example, any one or more of the following: a laser control system for controlling aspects of the generation and delivery of laser beams to the user; a displacement-based control system for controlling aspects of device 10 based on the determined displacement of device 10 across to the skin (e.g., as device is moved across the skin during treatment in a gliding mode or stamping mode), e.g., relative to a prior treatment position; a temperature control system; an eye safety control system to help prevent exposure of the eyes (e.g., the corneas) to the treatment radiation (an eye safety control system may be omitted in embodiments in which the laser radiation emitted from device 10 is inherently eye-safe); and/or a battery/power control system.

Control system 18 may include one or more sensors 26, user interfaces 28 for facilitating user interaction with device 10, and control electronics 30 for processing data (e.g., from sensors 26 and/or user interfaces 28) and generating control signals for controlling various components of device 10. Control electronics 30 may include one or more memory devices and processors for storing and executing logic instructions or algorithms or other data. Memory devices may include any one or more tangible, non-transitory device for storing electronic data (including logic instructions or algorithms), such as any type of RAM, ROM, Flash memory, or any other suitable volatile and/or non-volatile memory devices. Logic instructions or algorithms may be implemented as software, firmware, or any combination thereof. Processors may include any one or more devices, e.g., one or more microprocessors and/or microcontrollers, for executing logic instructions or algorithms to perform at least the various functions of device 10 discussed herein. Control electronics 30 may include exclusively analog electronics or any combination of analog and digital electronics.

Control system 18 may control components or aspects of device 10 based on feedback from sensors 26, user input received via user interfaces 28, and/or logic instructions/algorithms. For example, in some embodiments, control system 18 may control the operation of VCSEL(s) 14 based at least on feedback from a displacement sensor for detecting the displacement of device 10 relative to the skin 40 as the device is moved across the skin. Thus, for example, control system 18 may control VCSEL(s) 14 based on signals from a displacement sensor indicating that device 10 has moved a certain distance across target area 40 from a prior treatment position. As another example, control system 18 may control the operation of VCSEL(s) 14 based at least on feedback from a glide speed sensor for detecting the speed of device 10 moving across the skin. Thus, for example, control system 18 may control VCSEL(s) 14 based on signals from a glide speed sensor indicating that device 10 is moving at a particular speed across the skin 40.

More specifically, control system 18 may be configured to control one or more operational parameters of device 10. For example, control system 18 may control the treatment level (e.g., low power level, medium power level, or high power level) or treatment mode (e.g., gliding mode vs. stamping mode; or manually pulsed mode vs. automatically pulsed mode; or rapid-pulse mode vs. slow-pulse mode; or initial treatment mode vs. subsequent treatment mode; etc.), the performance of VCSEL(s) 14 (e.g., on/off, pulse-on time, pulse-off time, pulse duty cycle, pulse frequency, temporal pulse pattern, etc.), parameters of the radiation (e.g., radiation wavelength, intensity, power, fluence, etc.), the configuration or operation of one or more optical elements (e.g., the operation of a beam scanning system having rotating or otherwise moving optics or other elements), and/or any other aspects of device 10.

Sensors 26 may include any one or more sensors or sensor systems for sensing or detecting data regarding device 10, the user, the operating environment, or any other relevant parameters. For example, sensors 26 may include one or more of the following types of sensors: (a) one or more displacement sensor for determining the displacement of device 10 relative to the skin as device 10 is moved (e.g., glided) across the skin, (b) one or more glide speed sensor for determining the speed, rate, or velocity of device 10 moving (e.g., gliding) across the skin, (c) one or more skin-contact sensor for detecting proper contact between device 10 and the skin, (d) one or more pressure sensor for detecting the pressure of device 10 pressed against the skin, (e) one or more temperature sensor for detecting the temperature of the skin, a region of the skin, and/or components of device 10, (f) one or more radiation sensor for detecting one or more parameters of radiation (e.g., intensity, fluence, wavelength, etc.) delivered to the skin, (g) one or more color/pigment sensor for detecting the color or level of pigmentation in the skin, (h) one or more treatment endpoint sensor, e.g., a color/pigment sensor, for detecting an influence of the radiation on the skin (e.g., erythema, temperature, perifollicular edema, etc.) during or after a treatment, (i) one or more eye safety sensor for preventing unwanted eye exposure to light from VCSEL 14, (j) one or more dwell sensor for detecting if the device is stationary or essentially stationary with respect to the skin, (k) one or more roller-type sensors for detecting the displacement and/or glide speed of device 10, and/or any (l) other suitable types of sensors.

In some embodiments, control system 18 may include any of the various sensors and/or control systems disclosed in U.S. Ser. No. 13/366,246. For example, with reference to U.S. Ser. No. 13/366,246, control system 18 may include one or more displacement sensor 100 (e.g., displacement sensor 100A, 100B, 100C, or 100D), motion/speed sensor 102, skin-contact sensor 104, pressure (or force) sensor 106, temperature sensor 108, radiation sensor 110, color/pigment sensor 112, eye safety sensor 114, dwell sensor 116, and/or roller-based sensor 118, as disclosed in U.S. Ser. No. 13/366,246. As another example, again with reference to U.S. Ser. No. 13/366,246, control system 18 may include any or all of a VCSEL control system 130, a displacement-based control system 132, a user interface control system 134, a temperature control system 136, and/or a battery/power control system 138.

User interfaces 28 may include any systems for facilitating user interaction with device 10. For example, user interfaces 28 may include buttons, switches, knobs, sliders, touch screens, keypads, devices for providing vibrations or other tactile feedback, speakers for providing audible instructions, beeps, or other audible tones; or any other methods for receiving commands, settings, or other input from a user and providing information or output to the user. User interfaces 28 may also include one or more displays 32, one or more of which may be touchscreens for receiving user input. One or more user interfaces 28 or portions thereof may be included in a separate housing from the treatment device, such as in a smart charging dock or a personal computer, and the treatment device may communicate with the separate housing via hardwire (such as a cable or jack), wireless methods (such as infrared signals, radio signals, or Bluetooth), or other suitable communication methods.

Power supplies 20 may include any one or more types and instances of power supplies or power sources for generating or supplying power to the various components of device 10. For example, power supplies 20 may comprise one or more rechargeable or non-rechargeable batteries, capacitors, super-capacitors, DC/DC adapters, AC/DC adapters, and/or connections for receiving power from an outlet (e.g., 110V wall outlet). In some embodiments, power supplies 20 include one or more rechargeable or non-rechargeable batteries, e.g., one or more Li containing cells or one or more A, AA, AAA, C, D, prismatic, or 9V rechargeable or non-rechargeable cells.

VCSEL Radiation Source

FIG. 2 illustrates a side cross-sectional view of the structure of an example VCSEL chip 14. A laser cavity 102 is formed in the epitaxial growth direction with the active region 104 sandwiched between two multilayer dielectric mirror stacks 106 and 108 formed by several quarter-wavelength-thick semiconductor layers of alternating refractive indices formed on a substrate 110. These high reflectivity dielectric mirror stacks 106 and 108 are also referred to as distributed Bragg reflectors (DBR). The structure is typically connected to an n-type contact 112 and a p-type contact 114 at opposite sides of the structure.

FIG. 3A shows an example square-shaped VCSEL chip 14 mounted on a treatment device 10 (e.g., for laser hair removal), as viewed along the direction of the laser beam output shown in FIG. 2, i.e., the view of VCSEL 14 seen by the skin. FIG. 3A may be contrasted with FIG. 3B, which shows a corresponding view of a pair of edge-emitting laser diode bars mounted on a conventional treatment device.

Figure 4:
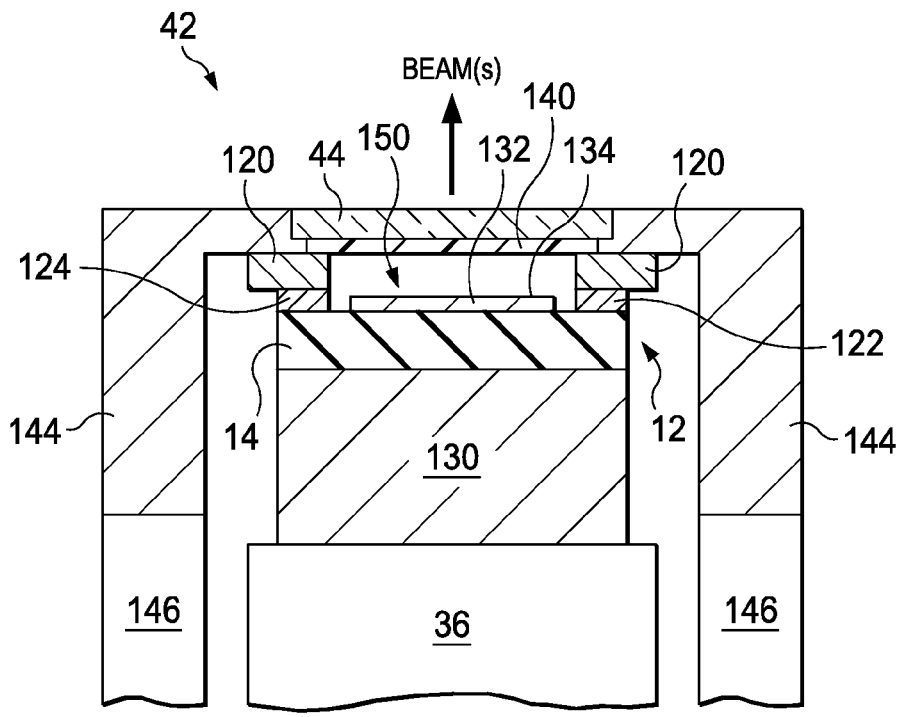
FIG. 4 illustrates a side cross-sectional view of the treatment tip of an example dermatological treatment device having a laser engine including a VCSEL chip arranged near the tip, according to an example embodiment.

FIG. 4 illustrates a side cross-sectional view of the treatment tip 42 of an example device 10 having a laser engine 12 including a VCSEL chip 14 arranged near the tip 42, according to an example embodiment. Some embodiments including this or a similar configuration may be configured as "direct exposure" and/or "close proximity" embodiments.

As shown, the laser engine 12 may include a VCSEL chip 14 coupled to a PCB contact 120 by an anode contact 122 and a cathode contact 124, and mounted to a heat sink 36. A heat spreader 130 may be coupled between the VCSEL chip 14 and the heat sink 36, to facilitate desired heat transfer away from the chip. The VCSEL chip 14 may include an array 132 of micro-emitters having an emitting surface 134.

A treatment window 44 and a diffuser 140 arranged behind the window 44 may be arranged downstream of the VCSEL 14, e.g., mounted to the PCB contact 120 as illustrated. The treatment window 44 and/or diffuser 140 may be secured to a treatment tip housing 144. In some embodiments, the treatment tip housing 144 may be thermally coupled to a separate heat sink 146 than the laser heat sink 36 (as shown in FIG. 4), or may be connected to the same heat sink 35, or may not be connected to any heat sink, or may be cooled (or heated) below (or above) skin temperature, e.g., using thermoelectric modules, cryogenic spray, refrigeration systems, resistive heaters, or any other suitable components.

In some embodiments, one or more sensors 26 may be mounted in the treatment tip 42, such as a displacement sensor, dwell sensor, skin temperature sensor, skin contact sensor, velocity sensor, or any of the other types of sensors 26 disclosed above. These sensors 26 may provide user feedback, may be responsive to user inputs, may control various parameters of the VCSEL 14 such as pulse timing, pulse duration, energy, power, etc., or may otherwise aid in safety, efficacy, usability or other purposes.

As shown, this configuration may define a cavity or air gap 150 between the VCSEL 14 and the treatment window 44 (or diffuser 140), and at least partially bounded on the sides by the various electrical contacts and/or other structures.

As discussed below, the beam profile(s) provided by the VCSEL can be defined by the configuration and/or control of the VCSEL itself, such that desired beam profile(s) can be directly transformed to the skin without additional optics 16. Thus, the VCSEL 14 can be configured for direct exposure (no optics between the VCSEL and the skin) and/or close proximity (less than 1 cm between the VCSEL emitting surface 134 and the target skin surface) radiation. For example, the VCSEL chip 14 may arranged such that the emitting surface 134 is in close proximity to the skin surface, e.g., less than less than 1 cm, less than 5 mm, less than 2 mm, less than 1 mm, less than 500 µm, less than 200 µm, or even less than 100 µm, with only a planar output window or film 44 to protect the emitting surface. For example, in some embodiments that include a diffuser 140 and a window 44, diffuser 140 has a thickness of between about 200 µm and about 1 mm, and window 44 has a thickness of between about 200 µm and about 2 mm. In a particular example embodiment, diffuser 140 has a thickness of about 0.4 mm, window 44 has a thickness of between about 1 mm, and gap 150 has a thickness of less than 0.5 mm, to define a proximity gap spacing of less than 2 mm.

In some embodiments, diffuser 140 may be configured to achieve approximately Lambertian angular profile for eye-safe radiation (e.g., Class 1M or better per IEC 60825-1). Other embodiments may omit the diffuser 64, thus resulting in a less scattered/more focused output beam, which may be suitable or advantageous for certain treatments, e.g., fractional treatments or ablative treatments.

In some embodiments, e.g., embodiments in which VCSEL is configured to generate a single combined beam, a mixer may be defined or arranged between the VCSEL 14 and the diffuser 140, which may be configured to distribute the light emitted by the VCSEL 14 before reaching the diffuser 140, and in some embodiments may provide a generally uniform distribution of light to the diffuser 140. The mixer could be a solid optical element (e.g., waveguide) arranged between VCSEL 14 and the diffuser 140, or could be an elongated hollow volume defined by a reflective wall, e.g., in the location of air gap 150. Some embodiments that include a mixer and diffuser may be configured to provide eye-safe radiation (e.g., Class 1M or better per IEC 60825-1).

In some embodiments, the output window 44 may be omitted, may be offset from the skin surface (e.g., set back from a leading surface of tip housing 144), may be non-planar, may be replaced by a thin coating that provides protection to the laser 14, and other alternatives. The high reflectivity of the VCSEL chip may promote throughput of photons to the skin by back-reflecting light remitted from the diffuser 140 (if present), the output window 44 (if present), and the skin back into the optical delivery path. In addition, the remainder of the cavity 150 may also be configured to increase throughput/re-radiation, for example, by including reflective sidewalls and a short path length between the laser 14 and diffuser 140 or between the laser 14 and the skin.

Unlike an edge-emitting laser bar, the output beam(s) from a VCSEL can be easily made inherently uniform due to the typically dense emitter distribution and the symmetrical beam divergence from each emitter. Thus, in some embodiments an additional optical mixer component for output beam transformation may be omitted, unlike certain edge-emitting laser bar systems.

As mentioned above, the radiation profile provided by the VCSEL 14, e.g., the beam profile(s) of one or more beams provided by the VCSEL, can be defined by the configuration and/or control of the VCSEL chip itself. For example, one or multiple emitter zones can be arbitrarily defined in the VCSEL and arranged in various shapes, to provide one or more discrete beams to the skin and having beam profile(s) defined by the configuration and operation of the emitter zones, as discussed below.

In some embodiments, a VCSEL micro-emitter array 132 may be divided into multiple groups or "zones" of micro-emitters, e.g., to provide multiple discrete beams for delivery to the skin (to form multiple discrete treatment spots on the skin, e.g., for fractional treatment), or to provide desired beam intensity profile(s) for one or more beams provided by the micro-emitter array 132, or both. The multiple micro-emitter zones may be independently addressable or controllable, e.g., by independently controlling the current applied to each zone, or may be collectively controlled.

In some embodiments, a micro-emitter array 132 includes multiple zones arranged to form a single combined beam, wherein different zones are driven differently (e.g., by different current levels, pulse timing parameters, etc.) such that different regions of the combined beam display differing intensities, thereby controlling the overall beam intensity profile of the combined beam, e.g., as discussed below with reference to FIGS. 8-10.

In other embodiments, a micro-emitter array 132 includes multiple zones that are sufficiently spaced apart to provide multiple discrete beams delivered to the skin, with each emitter zone providing a single beam to the skin, e.g., for fractional treatment, e.g., as discussed below with reference to FIGS. 11-17. In such embodiments, the emitter zones may be independently or collectively controlled, depending on the desired application. For example, the emitter zones may be independently controlled to successively activate the individual emitter zones to provide a sequence of beams to the skin at different locations on the skin corresponding to the different relative locations of the emitter zones on the VCSEL chip.

Single-Beam (Single-Zone or Multiple-Zone) VCSELs

Figure 5:
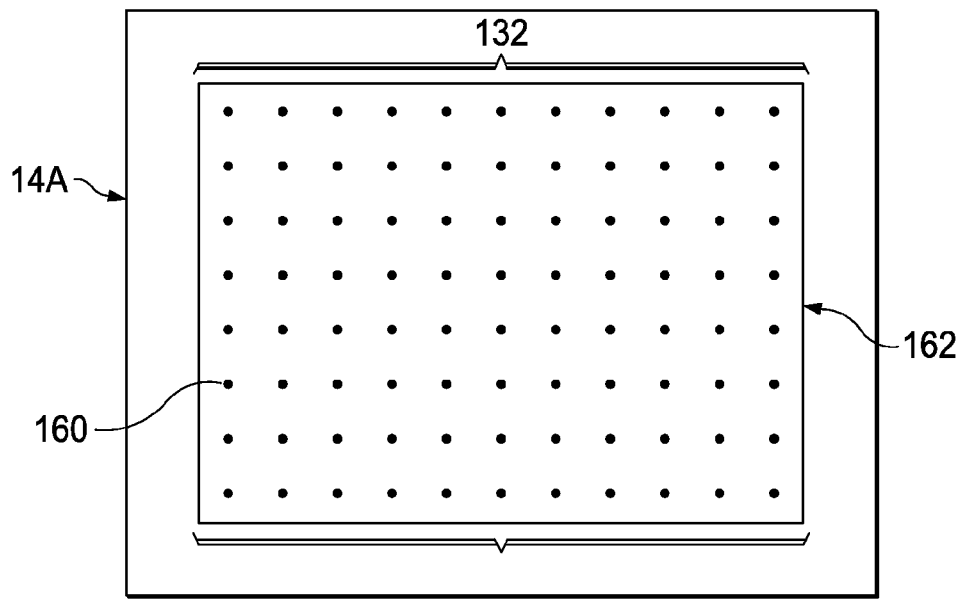
FIG. 5 shows an example VCSEL chip as viewed by the skin, showing an a 2-D array of micro-emitters defining a single emitter zone for delivering a single combined beam, according to an example embodiment.

FIG. 5 shows an example VCSEL chip 14A as viewed along the direction of the laser beam output shown in FIG. 2, i.e., the view of VCSEL 14A as seen by the skin. This example VCSEL chip 14A is configured with a single emitter zone to deliver a single collective beam to the skin. As shown, the VCSEL chip structure may define a 2-D array 132 of micro-emitters 160. Each micro-emitter 160 emits a slightly divergent micro-beam, which may combine with the micro-beams emitted by one or more other micro-emitter 160 due to the slight divergence (e.g., a 5-20 degree angle of divergence) of the micro-beams to form a collective beam for delivery to the skin, depending on the relative spacing between micro-emitters 160, the spacing between the emitting surface of the VCSEL and the skin (referred to herein as the "proximity gap spacing"), and/or other relevant factors. A group of micro-emitters 160 having micro-beams that combine to form a collective beam for delivery to the skin are referred to herein as a emitter zone 162.

In the example shown in FIG. 5, the VCSEL chip 14A includes a single emitter zone 162, such that the 2-D array of micro-emitters 160 cooperate to provide a single collective beam for delivery to the skin to form (at any point in time) a single treatment spot on the skin. In other embodiments, e.g., as discussed below with reference to FIGS. 11-17, a VCSEL 14 may be configured such that the array 132 of micro-emitters 160 defines multiple emitter zones 162 that provide multiple discrete collective beams for delivery to the skin to concurrently form multiple treatment spots on the skin, e.g., for a fractional treatment.

Figure 6:
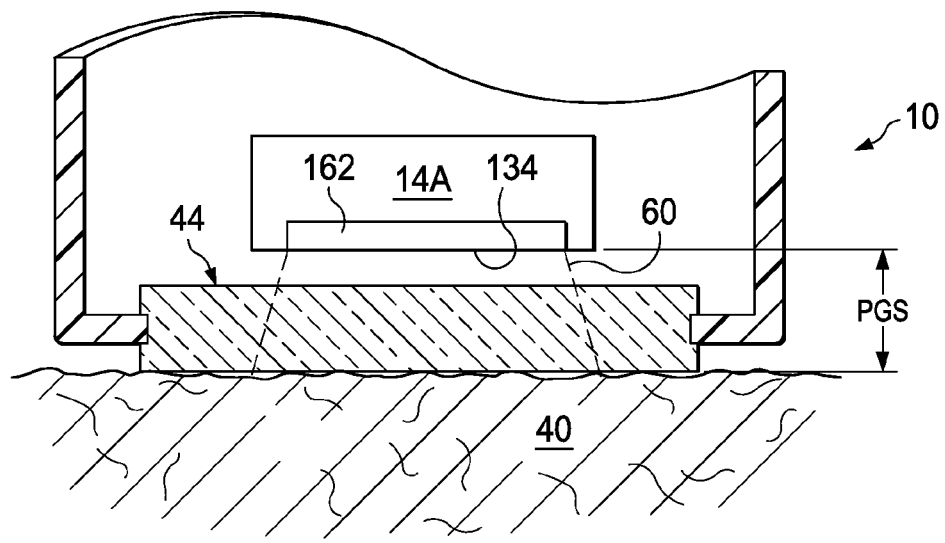
FIG. 6 illustrates a simplified cross-sectional side view of an example embodiment of device that includes a single-beam-source VCSEL configured to generate a single beam for providing a single treatment spot on the skin, and including a non-optic treatment window, according to an example embodiment.

FIG. 6 illustrates a simplified cross-sectional side view of an example embodiment of device 10 that includes the single-beam-source VCSEL 14A of FIG. 5 configured to generate a single beam for providing a single treatment spot on the skin. As discussed above, VCSEL 14A include an array 132 of micro-emitters 160 defining a single emitter zone 162, wherein the array of micro-emitter 160 emit an array of divergent micro-beams that combine (due to the divergence of the individual micro-beams) to form a single, generally uniform beam 60 for delivery to the skin, as shown in FIG. 6. Thus, in such embodiments, the micro-emitter array 132 acts as a single beam source to generate a single beam 130 that creates a single treatment spot on the skin. In this example arrangement, a transparent output window 44 is arranged between the VCSEL 14A and the skin, e.g., to protect VCSEL 14A from damage. In other embodiments the output window 44 is omitted.

Some embodiments are configured for close proximity radiation, i.e., where the proximity gap spacing (PGS) between the emitting surface 134 and the leading surface of the output window 44 is less than less than 1 cm. In some embodiments the PGS is less than 5 mm, less than 2 mm, less than 1 mm, less than 500 µm, less than 200 µm, or even less than 100 µm.

Figure 7:
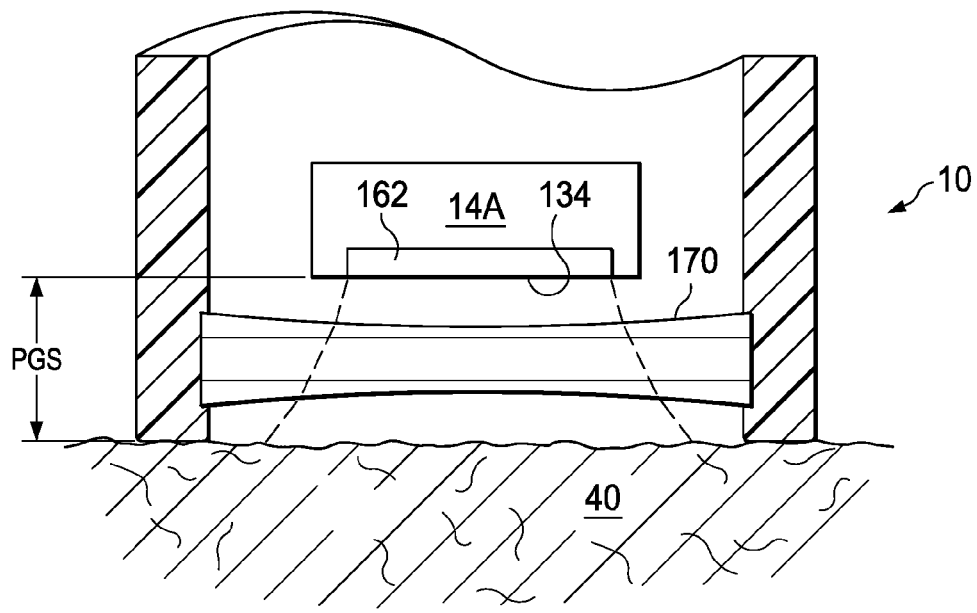
FIG. 7 illustrates a simplified cross-sectional side view of an example embodiment of device that includes a single-beam-source VCSEL configured to generate a single beam for providing a single treatment spot on the skin, and including an optic to influence the divergence of the beam, according to an example embodiment.

FIG. 7 illustrates a simplified cross-sectional side view of an example embodiment of device 10 that includes the single-beam-source VCSEL 14A of FIG. 5 and an optic 170 downstream of the VCSEL. Optic 170 may be any type of lens (e.g., concave, convex, ball lens, cylindrical lens, aspherical lens, etc.) or other optic element or elements for affecting the radiation emitted by VCSEL 14A as desired. For example, optic 170 may be provided e.g., to increase or decrease the divergence of the resulting beam 60 delivered to the skin, such as to provide a desired spot size or shape, energy intensity level at the skin, and/or to provide increased eye safety. In some embodiments, optic 170 may be provided directly on the VCSEL via coatings, MEMs structures or otherwise, and thus may be monolithic with the VCSEL. Other optics examples are a microlens array, fiber(s), or fiber bundles, among others.

Beam Intensity Profile Control

As discussed above, in some embodiments, individual micro-emitter zone 162 of a multi-zone (i.e., multi-beam-source) VCSEL may be independently addressable or controllable, e.g., by independently controlling the current applied to each zone 162. For example, zones 162 may be independently turned on/off or pulsed, pulsed with different timing parameters, or activated at different power levels. For pulsed embodiments, the various pulsing parameters for each zone 162, e.g., pulse on time, pulse off time, pulse frequency, pulse duration, pulse profile, intensity, power level, etc., may be controlled independent of the other zones 162. Thus, for instance, the multiple zones 162 may be controlled to deliver pulsed beams 60 (and create corresponding treatment spots) in any spatial or sequential order, e.g., according to a defined algorithm, semi-randomly, or randomly.

In embodiments in which emitter zones 162 are independently addressable, each zone 162 may be electrically connected to control electronics 30 by any suitable connections, e.g., lines 180 shown in FIG. 12 and discussed below. Control electronics 130 may include any suitable algorithms embodied as software, firmware, or other logic instructions that are executable by a processor to control one or more operational aspects of individual zones 162 (or groups of zones) via the respective electrical connections.

In some embodiments, an independently addressable multi-zone VCSEL may be configured to compensate for "edge effects" in the treatment zones (MTZs) generated by certain conventional laser treatment devices. It is well known that with certain laser sources (e.g., fiber laser, edge-emitting laser diode, solid-state laser like NdYAG), an output beam profile edge effect causes a central hot spot on the treatment skin, which may reduce the nominal effective fluence that can be delivered. Even when the as-designed output beam is perfectly uniform, the light scattering in the skin makes the beam profile edge less intense than the central portion.

Figure 8:
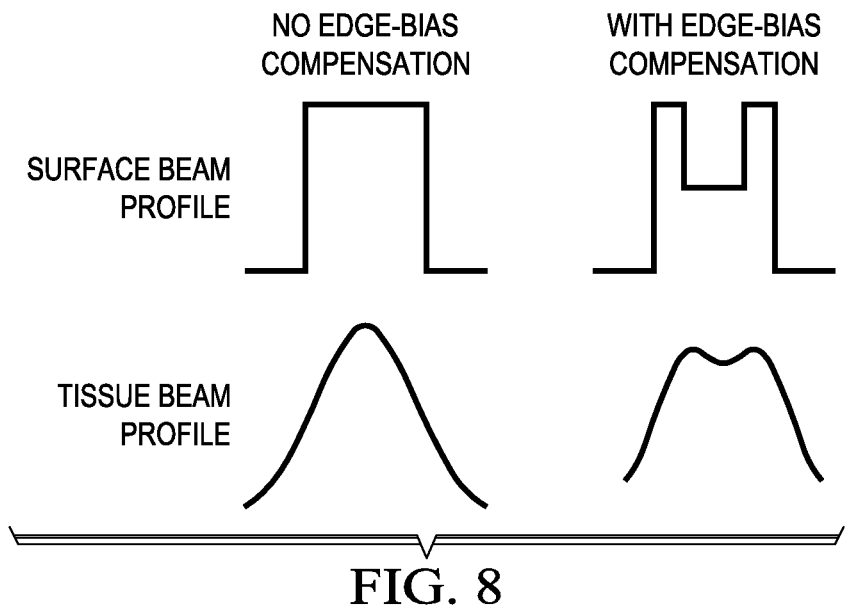
FIG. 8 shows the beam intensity profile incident at the skin surface (top) and at some depth within the skin tissue (bottom), as produced by a conventional laser (left) and by an independently addressable multi-zone VCSEL configured to compensate for edge-effects, according to an example embodiment.

FIG. 8 shows the beam intensity profile incident at the skin surface (top) and at some depth within the skin tissue (bottom), as produced by a conventional laser (left) and by an independently addressable multi-zone VCSEL configured to compensate for edge-effects, according to an example embodiment.

With reference to the beam delivered by a conventional laser (left side), as the initially uniform surface beam profile propagates down below the surface, the tissue scatters the light in all directions and causes a smearing effect. Therefore the sub-surface tissue beam profile becomes more Gaussian-like with a central peak. Since the treatment target is usually at least a fraction of millimeter for more below the surface, the actual treatment tissue beam profile is a smeared version of the original uniform surface profile. Even when the beam output from the device is perfectly uniform, the light scattering in the skin makes the beam profile edge less intense than the central portion. The central hot spot can be twice as intense (or more) than the edge portion. Thus, by deliberately biasing the surface edge intensity to be higher than that of the central region, the edge effects can be compensated and a more uniform sub-surface tissue beam profile can be generated for the intended treatment region.

Figure 9:
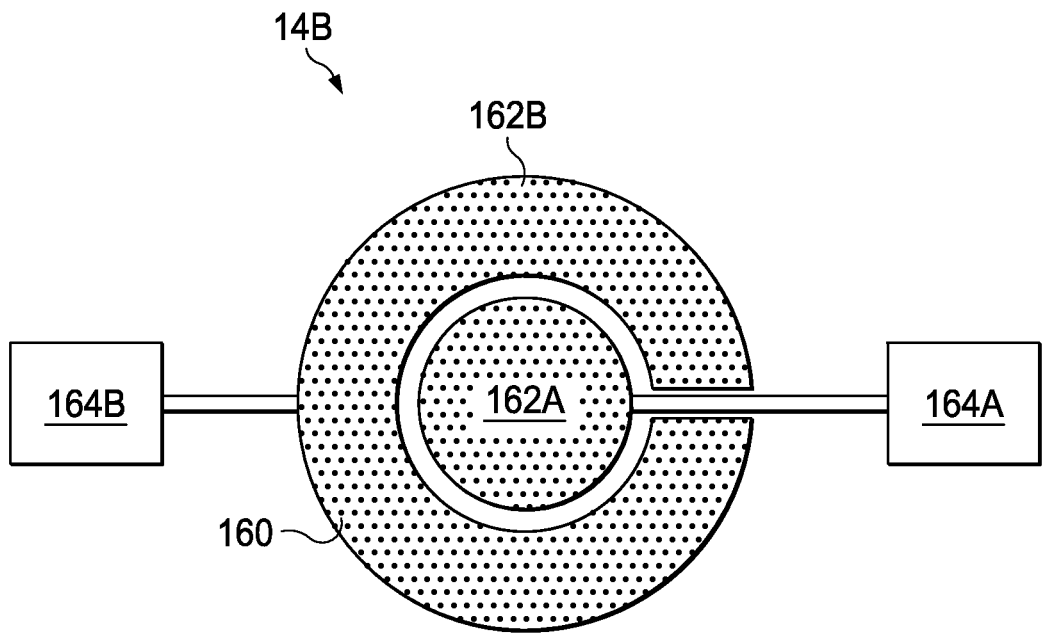
FIG. 9 illustrates an example multi-zone VCSEL having independently addressable, concentrically arranged emitter zones configured to compensate for edge effects in the sub-surface beam intensity profile.

FIG. 9 illustrates an example independently addressable multi-zone VCSEL 14B configured to compensate for such edge effects in the sub-surface beam intensity profile. VCSEL 14B is divided into two concentrically arranged micro-emitter zones 162: a central emitter zone 162A and an edge emitter zone 162B around the emitter zone 162A. The edge zone 162B can be driven with higher laser current via current source 164B than the central zone 162A via current source 164A to provide the beam intensity profile shown in the top right of FIG. 8. When this beam profile propagates below the tissue surface, the light scattering/smearing discussed above results in a more uniform tissue fluence distribution (e.g., a multi-peaked profile, or generally flat-topped profile), thus at least partially compensating for the edge effects and reducing or eliminating the central "hot spot." Reducing or even substantially eliminating such edge effects and centralized hot spot may allow treatment at a higher fluence. In other embodiments, a VCSEL may be configured with any other number (e.g., three, four, five, or more) concentrically arranged micro-emitter zones 162 to provide further compensation and tuning of the sub-surface intensity profile, e.g., to provide a substantially uniform sub-surface profile (i.e., flat-topped profile) or to provide any other desired intensity profile.

Figure 10:
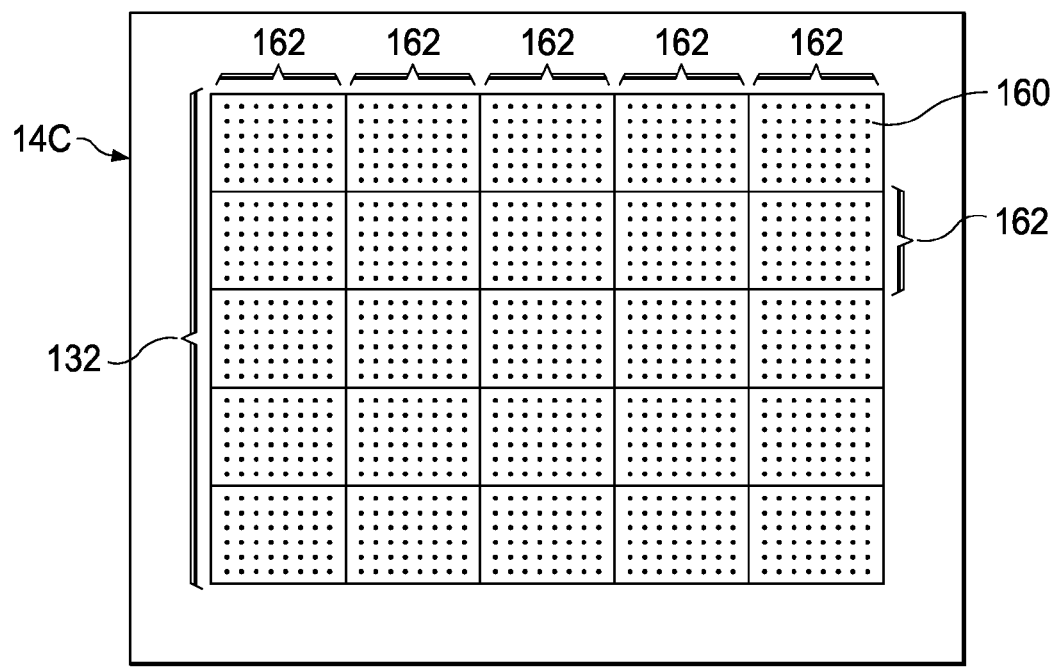
FIG. 10 illustrates another example of an independently addressable multi-zone VCSEL configured to compensate for edge effects as discussed above, or to provide any other desired beam intensity profile for a single combined beam, according to an example embodiment.

FIG. 10 illustrates another example independently addressable multi-zone VCSEL 14C configured to compensate for edge effects as discussed above, or to provide any other desired beam intensity profile for a single combined beam. As shown, example VCSEL 14C includes an array 132 of micro-emitters 160 divided into in a 2D array of discrete micro-emitter zones 162, each including a group of micro-emitters 160. The array 132 may be operated to provide a single combined beam (e.g., if all zones 162 are activated simultaneously), but each micro-emitter zone 162 may be individually controlled (e.g., by controlling the current applied to each zone 162) to provide a desired intensity profile, e.g., to provide a substantially uniform sub-surface profile as discussed above. Alternatively, the individual zones 162 may be activated at different times, e.g., to provide a successive sequence of beams from the different zones 162.

Multiple-Beam (Multiple-Zone) VCSELs

FIGS. 11-17 illustrate embodiments that include a VCSEL configured to generate an array (1D or 2D) of multiple discrete laser beams for creating an array (1D or 2D) of multiple spaced-apart treatment spots on the skin, e.g., to provide a fractional treatment.

Figure 11:
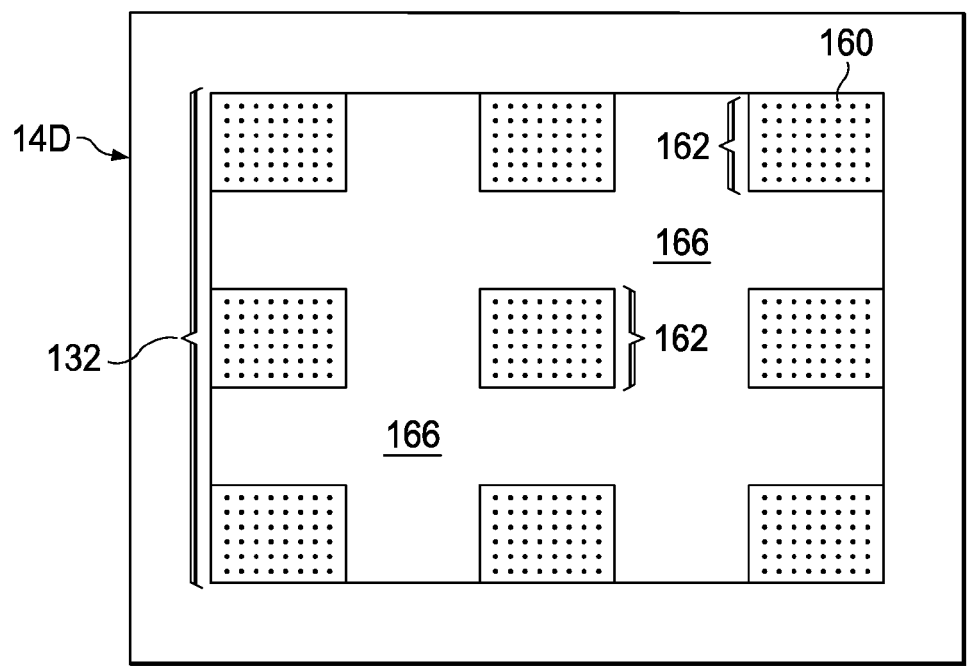
FIG. 11 illustrates an emitter surface view of an example VCSEL having an array of discrete micro-emitter zones configured to provide an array of discrete beams to the skin, e.g., providing a fractional treatment, according to an example embodiment.

FIG. 11 illustrates an emitter surface view of an example VCSEL 14D in which micro-emitters 160 are arranged in a 2D array (in this example, a 3×3 two-dimensional array) of discrete micro-emitter zones 162, each including a number of micro-emitters 160. Each micro-emitter zone 162 acts as a single beam source to provide a single discrete beam 60 for delivery to the skin. In particular, the micro-beams emitted by the micro-emitters 160 in each particular zone 162 combine (due to the divergence of the individual micro-beams) to form a single, discrete beam 60. Thus, the 3×3 array of discrete spaced-apart micro-emitter zones 162 forms a 3×3 array of discrete beam sources that generate a 3×3 array of discrete spaced-apart beams 60, which provide a corresponding 3×3 array of discrete spaced-apart treatment spots 62 on the skin, e.g., for providing a fractional treatment.

The micro-emitter zones 162 may be separated from each by non-active regions 166 of the VCSEL chip, which regions may be formed by known photolithographic techniques. Each micro-emitter zone 162 may have any shape and size, and may include any number of micro-emitters 160 arranged in any suitable pattern to form any suitable one-dimensional or two-dimensional array of micro-emitters 160. For example, in some embodiments in which VCSEL is configured for pulsed radiation, each zone 162 may be shaped to provide a desired treatment spot size and/or shape, taking into consideration an assumed rate of movement of the device 10 across the skin during the pulsed radiation. Thus, for instance, to provide treatment spots 62 having a generally symmetrical shape (e.g., generally circular or square), each zone 162 may be elongated in the direction perpendicular to the expected glide direction of the device 10, with the aspect ratio of such elongation being selected based on an expected glide speed or range of glide speeds of the device 10. The zones may also be created by masking certain regions, such as by overlaying an opaque material, or by using optics, such as microlens array, or any other suitable means. As with uniform VCSELs, optics may be monolithic to the VCSEL and built with coatings, such as spun-on-glass, or MEMs, or other means.

Further, as discussed above regarding the single-beam-source VCSEL, the micro-emitters 160 in an array 132 may be evenly spaced from each other, e.g., to provide a beam 60 having a generally uniform intensity profile, or may be unevenly spaced from each other, e.g., to provide a beam 60 having a selected non-uniform intensity profile suitable for a particular application or treatment.

In addition, it should be understood that the illustrated 3×3 array of zones 162 is for illustration purposed only and that a VCSEL may be configured with an n1 by n2 array of zones 162, wherein n1 and n2 are any suitable numbers, and that such zones 162 may be arranged in any suitable pattern to form any suitable one-dimensional or two-dimensional array of zones 162. Zones 162 may evenly spaced from each other, e.g., to provide a generally uniform array of beams 60, or may be unevenly spaced from each other, e.g., to provide a non-uniform array of beams 60 for a particular application or treatment.

Further, each zone 162 may have any suitable shape and size. For example, each zone 162 may be a diameter of between 80 µm and 500 µm, which may be suitable for a fractional treatment, for example. Other embodiments may include smaller or larger zones 162.

Figure 12:
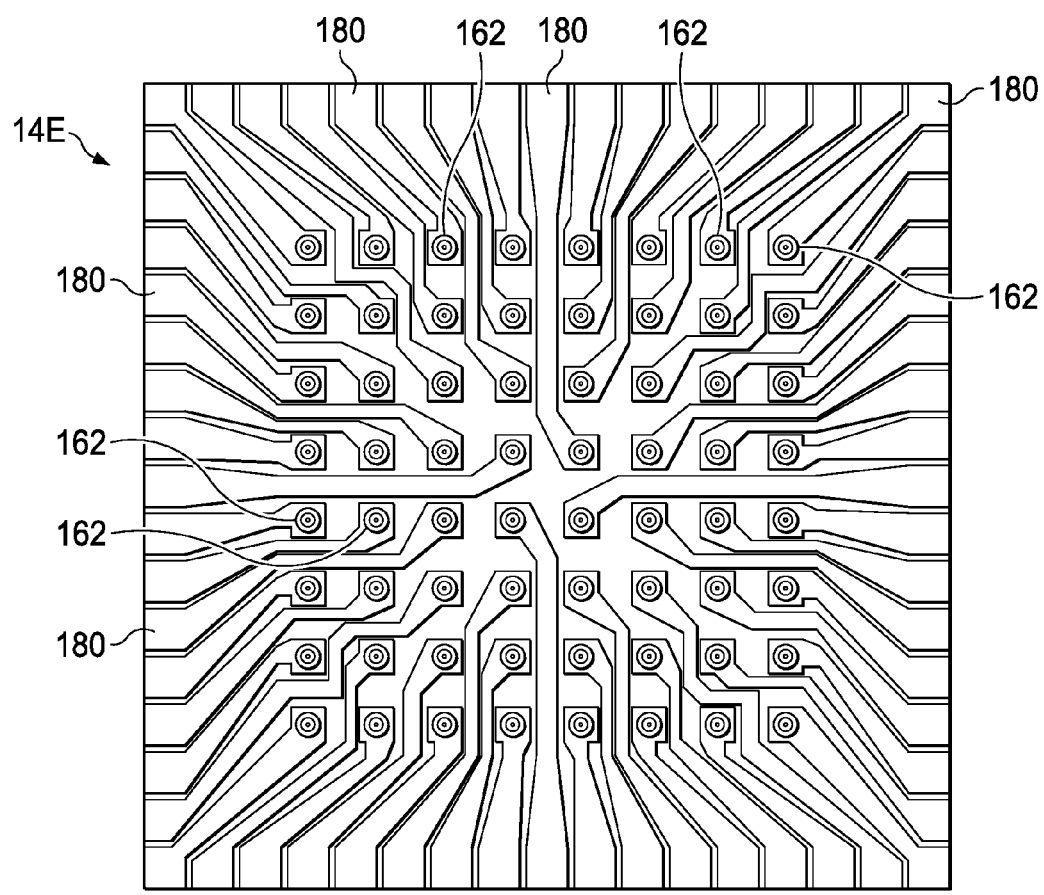
FIG. 12 illustrates another example of an independently addressable multi-zone VCSEL having an array of spaced-apart micro-emitter zones for providing an array of discrete beams to the skin, according to an example embodiment.

FIG. 12 illustrates an example independently addressable multi-zone VCSEL 14E having an array of spaced-apart micro-emitter zones 162 for providing an array of discrete beams to the skin, e.g., similar to VCSEL 14D of FIG. 11. In particular, FIG. 12 shows an example design for independently addressing the micro-emitter zones 162, wherein each zone 162 is addressed by a conductive line 180. Each conductive line 180 may be isolated from all other lines 180 such that each zone 162 may be addressed individually, or particular lines 180 may be connected to one or more other lines 180 such that multiple zones 162 may be addressed together.

Figure 13:
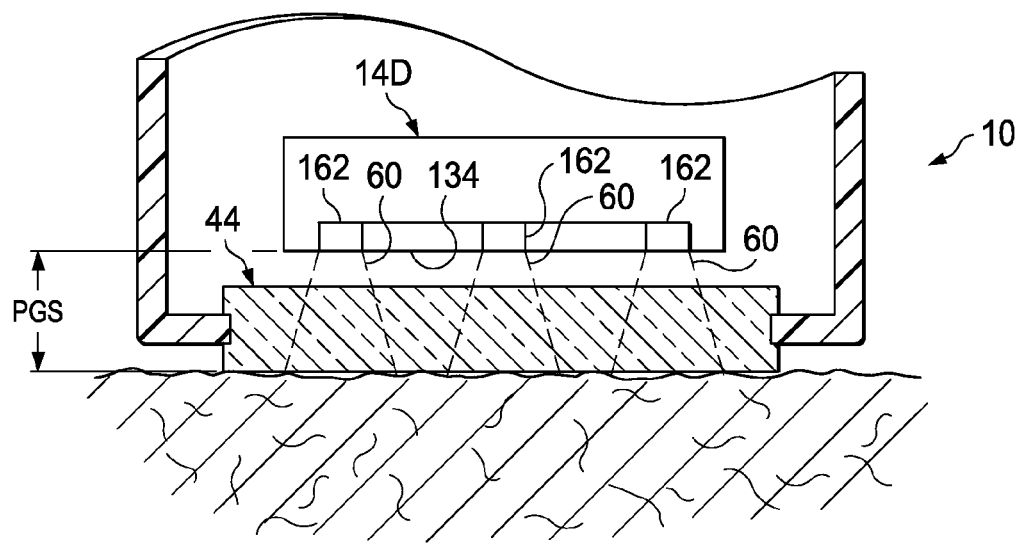
FIG. 13 illustrates a simplified cross-sectional side view of an example embodiment of device that includes the example multi-beam VCSEL of FIG. 11, and including a non-optic treatment window, according to an example embodiment.

FIG. 13 shows a simplified cross-sectional side view of an example embodiment of device 10 that includes the example multi-beam VCSEL 14D of FIG. 11. In particular, the figure shows one row of the 3×3 array of micro-emitter zones 162, which row generates three discrete, spaced-apart beams 60 for delivery to the skin. In this example arrangement, a transparent output window 44 is arranged between the VCSEL 14D and the skin, e.g., to protect VCSEL 14D from damage. In other embodiments the output window 44 is omitted. Some embodiments are configured for close proximity radiation, i.e., where the proximity gap spacing (PGS) between the emitting surface 134 and the leading surface of the output window 44 is less than less than 1 cm. In some embodiments the PGS is less than 5 mm, less than 2 mm, less than 1 mm, less than 500 µm, less than 200 µm, or even less than 100 µm.

Figure 14:
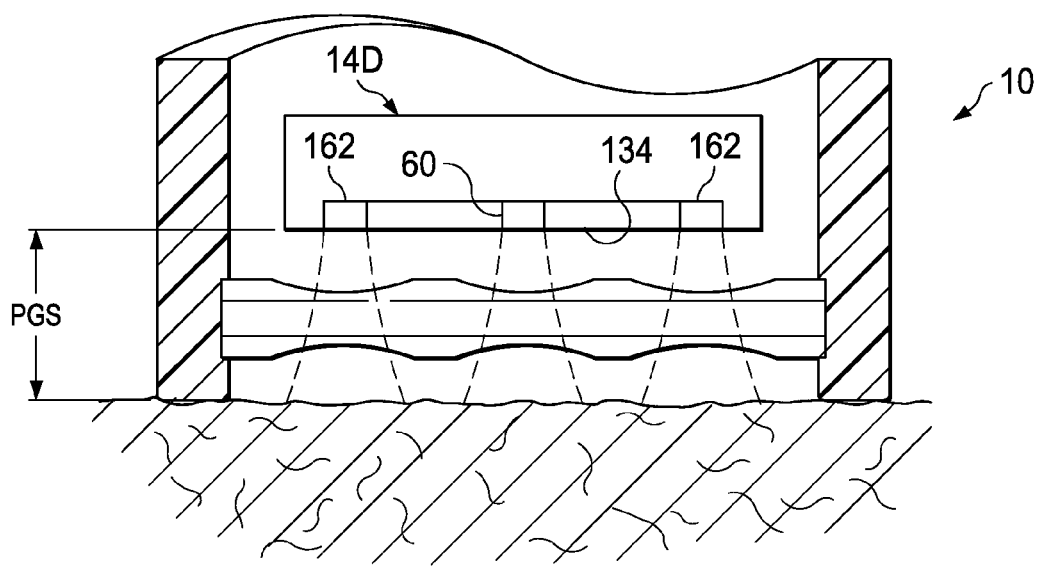
FIG. 14 illustrates a simplified cross-sectional side view of an example embodiment of device that includes the example multi-beam VCSEL of FIG. 11, and including a micro-lens array, according to an example embodiment.

FIG. 14 a simplified cross-sectional side view of an example embodiment of device 10 that includes the multi-beam-source VCSEL 14D of FIG. 11, with a micro-lens array 172 for affecting each beam 60 generated by the various micro-emitter zones 162. Micro-lens array 172 may include an array of optical elements corresponding to the array of micro-emitter zones 162 of the particular VCSEL 14D, with each optical element of the array corresponding to one zone 162 of VCSEL 14D (and thus one beam 60). The optical elements of the micro-lens array 172 may be discrete elements or may be formed as a contiguous structure, e.g., as shown in FIG. 10. Each optical element of the array 172 may comprise any type of lens (e.g., concave, convex, ball lens, cylindrical lens, aspherical lens, etc.) or other optic for affecting the corresponding beam 60 as desired. For example, each optical element of array 172 may be provided to increase or decrease the divergence of the resulting beam 60 delivered to the skin, such as to provide a desired spot size or shape, energy intensity level at the skin, and/or to provide increased eye safety. Some embodiments are configured for close proximity radiation, i.e., where the proximity gap spacing (PGS) between the emitting surface 134 and the leading surface of the output window 44 is less than less than 1 cm, e.g., less than 5 mm, less than 2 mm, less than 1 mm, less than 500 µm, less than 200 µm, or even less than 100 µm.

Figure 15:
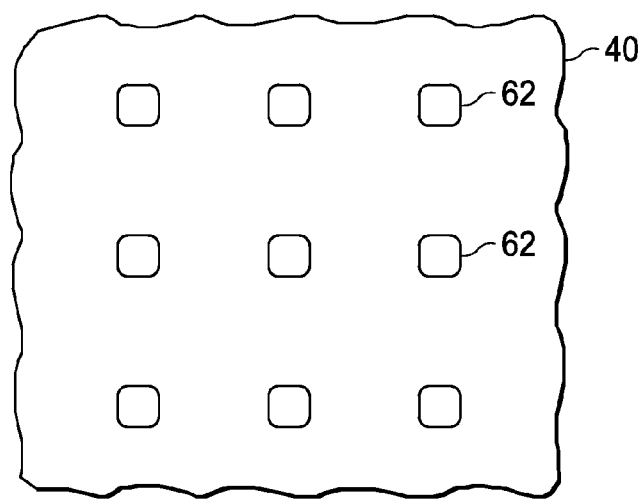
FIG. 15 illustrates an example two-dimensional array of treatment spots generated on the skin by the example multi-beam VCSEL of FIG. 11 according to an example embodiment.
Figure 16:
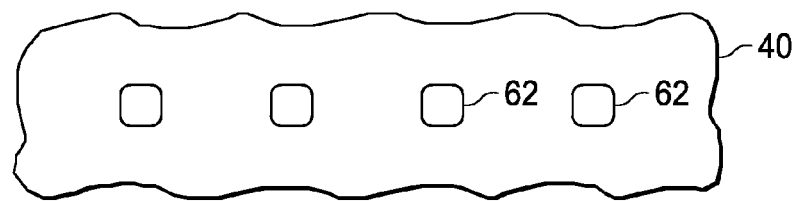
FIG. 16 illustrates an example one-dimensional array of treatment spots generated by an example VCSEL having a one-dimensional array of micro-emitter zones, according to an example embodiment.

FIG. 15 illustrates an example array of treatment spots 62 generated on the skin by the example VCSEL 14D shown in FIG. 11. FIG. 16 illustrates an example one-dimensional array of treatment spots 62 generated by another example VCSEL having a one-dimensional array of (in this example, four) micro-emitter zones 162. As discussed above, VCSEL(s) may be configured to provide any other suitable one-dimensional or two-dimensional array of treatment spots 62 by defining, configuring, and operating micro-emitter zones 162 as desired.

For at least some VCSELs, each micro-emitter 160 emits a circularly symmetrical micro-beam. For example, each micro-emitter 160 may emit a micro-beam having an axially-symmetric divergence angle of above 20° (e.g., conventional VCSELs), or a divergence angle of between 10° and 20° (e.g., certain surface relief and antiresonant reflecting optical waveguide structures), or a divergence angle of between 7° and 10°, or a divergence angle of below 7° (e.g., certain holey structures, such as photonic crystals and multi-leaf structures), or a divergence angle of about 6° (e.g., certain multi-leaf VCSELs), or a divergence angle of below 6°, e.g., between 5.1° and 5.5° (for certain photonic crystal vertical-cavity surface-emitting laser (PC-VCSEL)), e.g., as described in "*Reduction of the Far-Field Divergence Angle of an 850 nm Multi-Leaf Holey Vertical Cavity Surface Emitting Laser,*" Zhou Kang et al., CHIN. PHYS. LETT. Vol. 28, No. 8 (2011) 084209; and "*Reduced divergence angle of photonic crystal vertical-cavity surface-emitting laser,*" Anjin Liu et al., Appl. Phys. Lett. 94, 191105 (2009); doi:10.1063/1.3136859.

As discussed above, the micro-emitter array 132 of each particular VCSEL may have any suitable shape, size, and configuration, and may include any suitable number of micro-emitters 160 arranged in any suitable pattern to form any suitable one-dimensional or two-dimensional array 132. For example, the micro-emitters 160 in an array 132 may be evenly spaced from each other, e.g., to provide a beam 130 having a generally uniform intensity profile, or may be unevenly spaced from each other, e.g., to provide a beam 130 having a selected non-uniform intensity profile suitable for a particular application or treatment. For example, micro-emitters 160 towards the outside of the array 132 may be spaced further apart from each other to provide a more rounded (i.e., less flat-topped or top hat-like) beam intensity profile, which may be suitable for particular applications or treatments. As another example, micro-emitters 160 towards the inside of the array 132 may be spaced further apart from each other to provide a more intensity flat-topped profile, or a cusped profile having a dip in intensity level near the center of the profile, which may be suitable for particular applications or treatments. Micro-emitters 160 and micro-emitter zones 162 may be arranged and operated in any other suitable manner to provide any other desired beam intensity profile.

As another example, the micro-emitter array 132 of a VCSEL may define multiple "multiple-zone, single-beam" arrangements, e.g., the concentric dual-zone arrangement shown in FIG. 9, which arrangements may be spaced apart to provide multiple beams to the skin. Thus, a single VCSEL may deliver an array of discrete beams, each having a beam intensity profile defined or controlled by the respective arrangement. For example, a VCSEL may be configured to deliver an array of generally flat-topped beams to the skin, e.g., for a fractional treatment.

Some embodiments that utilize a multiple-beam VSCEL (or multiple single-beam or multiple-beam VCSELs) may include optics 16 configured to modify the relative spacing or position of the multiple beams, e.g., to provide a desired spacing or relative positioning of treatment spots on the skin.

Figure 17:
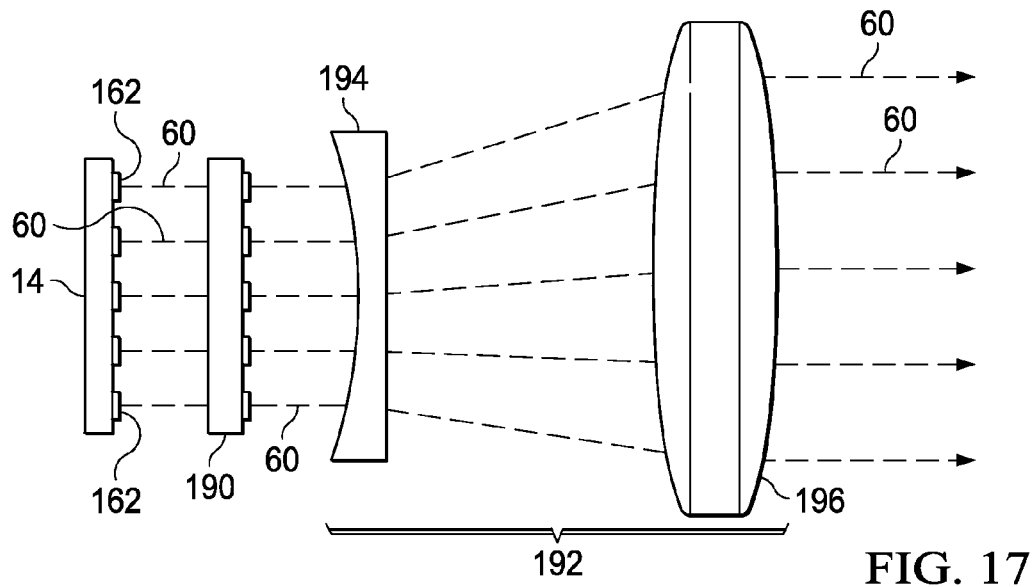
FIG. 17 illustrates an example arrangement of optics for increasing the relative spacing between multiple beams produced by a multi-beam VCSEL for delivering multiple discrete beams to the skin, e.g., providing a fractional treatment, according to an example embodiment.

FIG. 17 illustrates an example arrangement of optics 16 for increasing the relative spacing between multiple beams produced by a VSCEL 14 having an array of emitter zones 162 configured to deliver multiple discrete beams (e.g., VSCEL 14D or 14E discussed above). As shown, the arrangement may include a (optional) Fresnel micro-lens plate 190 followed by beam spacing optics 192 including lens elements 194 and 196 to increase the relative spacing between the array of beams 60 before delivery to the skin.

Thus, using VCSEL lasers in a dermatological device 10 may provide various beneficial aspects. Some of these aspects that may be incorporated in various embodiments of dermatological treatment device 10 are summarized below.

For example, VCSEL(s) may provide a densely packed 2-D array of micro-emitters, which enables spatially uniform beam output for large area exposure. This may eliminate the need of an optical mixer for output beam profile homogenization. This may also enhance eye safety (e.g., as compared to an edge emitter laser) by eliminating concentrated, high-intensity output regions.

As another example, the VCSEL chip shape and configuration can directly define the output beam intensity profile, as discussed above. Thus, a specific treatment spot pattern may be generated as desired.

As another example, the axial symmetric beam divergence from VCSEL micro-emitters enables both micro- and macro-lensing with simple spherical lenses, e.g., in embodiments in which beam conditioning is suitable or desired.

As another example, the smaller divergence angle (about 5° to about 20°) relative to the large fast-axis divergence (about 40°) in an edge-emitting laser bar reduces the rate of beam spread and thus enables a larger proximity gap spacing (PGS) between the laser and the treatment target for direct exposure (e.g., no optics or minimal optics between the VCSEL emitting surface and the skin) and/or close proximity arrangement (less than 1 cm between the VCSEL emitting surface and the skin surface). For an equivalent beam spread at the target surface, the proximity gap spacing for a VCSEL source can be about three times as large as compared to an edge-emitting laser diode (with respect to the fast-axis direction). Thus, mechanical design tolerance may thus be less of a concern, e.g., as compared to devices that employ edge emitter laser diodes.

As another example, due to the inherent high output coupler reflectivity (e.g., greater than 99%) of the distributed Bragg reflectors in certain VCSELs (e.g., as compared to less than 5% for the edge emitting laser bar), effective skin target fluence due to photon back-reflection from the highly reflective emitting surface can be greatly enhanced.

As another example, the output power of VCSELs has a lower temperature sensitivity (e.g., about 30% lower) as compared to a typical edge-emitting laser bar. This may enable the VCSEL to operate at a higher temperature with lower power loss, which may be particularly advantageous in a self-contained handheld battery powered device where cooling capacity may be limited.

As another example, in certain VCSELs the electrical contact is decoupled from the thermal contact, which may simplify the thermal management and the laser engine packaging. In some embodiments, the associated reduction of soldering and the associated flux cleaning near the laser facet may reduce the chance of facet damage in the assembly process and enhance the laser engine assembly yield.

As another example, VCSELs may provide an electrical advantage for better power efficiency, e.g., as compared with edge-emitting laser diodes. It is relatively simple to construct any electrical connectivity among various emitter zones 162 of a VCSEL through the lithographically defined metallization of the VCSEL fabrication process. Different zones 162 can be connected electrically in series or parallel. In a battery-powered handheld device 10, this allows one to more closely match the total forward diode voltage drop to the battery voltage source. This may be especially applicable for matching InP material system with wavelength greater than 1400 nm where the laser emitter operating voltage is below 1.5V, significantly less than that of a typical Li-ion battery cell voltage of more than 3V. In this case, it may be advantageous to connect two laser emitter zones in series to minimize the power dissipation in the laser drive current control FET and therefore maximize the battery efficiency.

As another example, the ability to create independent emitter zones 162 allows the beam intensity profile to be controlled in real-time through electrical means. Each zone 162 can be driven independently to achieve a desired intensity profile optimized for a given treatment and can even be varied (manually or automatically) during a particular treatment and/or between treatments, e.g. according to a defined protocol or based on feedback from one or more sensors 26.

As another example, the VCSEL emission zones can be grouped into a spatially separated 2-D array for an all-solid-state fractional treatment device. The emission zones can also be collimated or focused with a single Fresnel micro-lens plate.

In some embodiments, device 10 having one or more VCSELs 14 may be configured for large area dermatological treatments, e.g., hair removal. Unlike with an edge-emitting laser bar, the output beam from certain VCSELs is inherently uniform due to the dense emitter distribution and symmetrical beam divergence. Thus, in contrast to certain edge-emitting laser bar systems, an optical mixer component for output beam transformation may be omitted. The beam profile can be designed on the VCSEL laser chip itself.

In other embodiments, device 10 having one or more VCSELs 14 may be configured as an all-solid-state 2-D array fractional treatment device. Spatially separated emitter zones, e.g., with diameter ranging from about 80 to 500 µm, can be created in a single integrated VCSEL chip as discussed above. Each zone can also be driven separately. This enables, for example, a 2-D emitter array for fractional laser treatment, where each emitter zone generates a denatured micro-thermal-zone (MTZ) surrounded by healthy tissue for regrowth. In some embodiments, the 2-D emitter array can also be lensed with a Fresnel micro-lens plate followed by beam spacing optics to cover a large treatment large area, e.g., as discussed above with respect to FIG. 17. Concurrent exposure of many MTZs (e.g., several hundred MTZs) can thus be achieved without any scanning optics.

In other embodiments, VCSELs may be utilized as the radiation source in any suitable dermatological treatment device for providing any suitable dermatological treatment, e.g., hair removal, skin rejuvenation, wrinkle treatment, acne treatment, treatment of vascular lesions (e.g., spider veins, diffuse redness, etc.), treatment of cellulite, treatment of pigmented legions (e.g., age spots, sun spots, moles, etc.), tattoo removal, and various other treatments. For example, VCSELs may be utilized as the radiation source in any of the various embodiments and configurations, incorporating any of the various features, functionality, and operational aspects, and for providing any of the various treatments as disclosed in any of the following: U.S. Pat. Nos. 7,452,356; 7,250,045; 7,118, 563; 7,413,567; 7,981,111; U.S. patent application Ser. Nos. 12/607,280; 12/554,872; 12/772,104; 11/157,275; 11/545, 963; 11/829,747; 12/137,452; 12/137,263; 12/189,079; 12/193,544; 12/271,819; 12/430,730; 12/554,831; 13/366, 202; 13/366,237; 13/366,246; 13/366,256; 13/366,154; 13/366,177; U.S. Provisional Patent Application Nos. 61/533,786; 61/533,172; 61/533,641; 61/533,677; 61/469, 316; 61/545,481; 61/594,128; 61/563,491; 61/600,951; and 61/590,559; all of which disclosures are herein incorporated by reference in their entirety.

The invention claimed is:

1. A device for providing laser-based dermatological treatments, the device comprising:
    a device body having an application end;
    a VCSEL chip supported in the device body, the VCSEL chip including an array of multiple micro-emitters formed integrally on a common substrate of a monolithic chip, each micro-emitter configured to emit a micro-beam, wherein the array of micro-emitters defines multiple emitter zones on the chip, each emitter zone comprising one or more of the micro-emitters;
    wherein at least two of the multiple emitter zones on the VCSEL chip are configured such that, with the application end of the device positioned in contact with the skin, the micro-beams emitted by the micro-emitters of the at least two emitter zones collectively form a single combined beam at an output plane or surface at the application end of the device, which combined beam from the at least two emitter zones forms a single treatment spot on the skin;
    a processor; and
    computer instructions stored in a non-transitory computer-readable medium and executable by the processor to control the at least two emitter zones on the VCSEL chip independently such that the micro-beams emitted by the micro-emitters of the at least two emitter zones collectively form the single combined beam at the output plane or surface at the application end of the device, which combined beam forms the single treatment spot on the skin.

2. The device of claim 1, wherein controlling the at least two emitter zones independently comprises controlling at least one operational parameter of the at least two emitter zones independently.

3. The device of claim 1, wherein the computer instructions are executable to control the at least two emitter zones independently to provide a non-uniform beam intensity profile.

4. The device of claim 1, wherein the computer instructions are executable to supply different currents to the at least two emitter zones.

5. The device of claim 1, wherein the at least two emitter zones are arranged concentrically.

6. The device of claim 5, wherein the computer instructions are executable to supply a larger current to a concentrically outer emitter zone as compared to a concentrically inner emitter zone.

7. The device of claim 1, wherein the at least two emitter zones comprise a two-dimensional rectangular array of emitter zones.

8. The device of claim 1, wherein the at least two emitter zones comprise at least three emitter zones.

9. The device of claim 1, wherein the micro-emitters of different emitter zones are arranged with different packing densities.

10. The device of claim 1, wherein the computer instructions are executable to:
    activate the emitter zones in a pulsed manner; and
    independently control one or more pulse parameters of the at least two emitter zones.

11. The device of claim 1, wherein the VCSEL chip includes:
    a first set of multiple emitter zones configured to form a first combined beam through the application end of the device, which first combined beam forms a first treatment spot on the skin; and
    a second set of multiple emitter zones configured to form a second combined beam through the application end of the device, which second combined beam forms a second treatment spot on the skin;
    wherein the computer instructions are executable to:
        control the first set of multiple emitter zones independently of each other; and
        control the second set of multiple emitter zones independently of each other.

12. The device of claim 11, wherein the computer instructions are executable to supply different currents to the at least two emitter zones.

13. The device of claim 1, wherein the device includes no optics downstream of the VCSEL chip.

14. The device of claim 13, further comprising a window or film downstream of the VCSEL chip.

15. The device of claim 1, wherein the computer instructions are executable ed to pulse the multiple emitter zones of the VCSEL chip to emit a sequence of pulsed beams to the skin to generate an array of treatment spots on the skin.

16. The device of claim 1, wherein:
    the VCSEL chip has an emitter surface; and
    the emitter surface is arranged such that when the application end is in contact with the skin, the emitter surface is spaced from the skin surface by less than 10 mm.

17. The device of claim 1, wherein:
    the VCSEL chip has an emitter surface; and
    the emitter surface is arranged such that when the application end is in contact with the skin, the emitter surface is spaced from the skin surface by less than 2 mm.

18. The device of claim 1, wherein the combined beam provided by the multiple emitter zones is divergent in at least one direction upon incidence with the skin surface.

19. A method for providing a laser-based dermatological treatment, the method comprising:
    providing a device having a VCSEL chip supported in the device body, the VCSEL chip including an array of multiple micro-emitters formed integrally on a common substrate of a monolithic chip, each micro-emitter configured to emit a micro-beam, wherein the array of micro-emitters defines multiple emitter zones on the chip, each emitter zone comprising one or more of the micro-emitters, wherein at least two of the multiple emitter zones on the VCSEL chip are configured such that the micro-beams emitted by the micro-emitters of the at least two emitter zones collectively form a combined beam through an application end of the device, positioning the device such that the application end of the device is in contact with a target area of skin; and with the device positioned such that the application end is in contact with the target area of skin, using electronics coupled to the at least two emitter zones of the VCSEL chip to control the at least two emitter zones independently such that the micro-beams emitted by the micro-emitters of the at least two emitter zones collectively form the combined beam through the application end of the device, which combined beam forms a single treatment spot on the skin.

20. A VCSEL laser package for use in a device for providing radiation-based dermatological treatments, comprising:

a VCSEL chip including an array of micro-emitters formed integrally on a common substrate of a single monolithic chip, each micro-emitter configured to emit a micro-beam;

wherein the array of micro-emitters on the VCSEL chip is divided into multiple emitter zones on the single monolithic chip, each emitter zone comprising one or more of the micro-emitters;

wherein at least two of the multiple emitter zones on the single monolithic chip have separate control interfaces such that the at least two emitter zones are independently addressable via the separate control interfaces;

a processor; and computer instructions stored in a non-transitory computer-readable medium and executable by the processor to independently control the at least two emitter zones on the VCSEL chip by applying different currents to the at least two emitter zones via the separate control interfaces of the at least two emitter zones;

wherein the micro-beams emitted by the micro-emitters of the at least two emitter zones collectively form a single combined beam downstream of the VCSEL chip; and wherein the independent control of the at least two emitter zones by applying the different currents to the at least two emitter zones influences a beam profile of the single combined beam collectively formed by the at least two emitter zones of the VCSEL chip.

21. The device of claim 1, wherein the multiple emitter zones of the VCSEL chip are configured to generate multiple discrete treatment spots on the skin simultaneously, the multiple discrete treatment spots being spaced apart from each other on the skin by areas of non-irradiated skin.

22. The device of claim 1, further comprising computer instructions executable to automatically pulse the micro-emitters provided on the VCSEL chip while the device is moved across the skin to generate a row of treatment spots on the skin in the direction of movement of the device, each pulse generating one of the treatment spots in the row and each treatment spot being spaced apart from each other treatment in the row by areas of non-treated skin.

23. The VCSEL laser package of claim 20, wherein the multiple emitter zones on the single VCSEL chip are configured to generate multiple discrete treatment spots on the skin, the multiple discrete treatment spots being spaced apart from each other on the skin by areas of non-irradiated skin, with each emitter zone generating a single discrete treatment spot on the skin.

24. The VCSEL laser package of claim 20, wherein the micro-emitters provided on the single VCSEL chip are configured to be automatically pulsed while the device is moved across the skin to generate a row of treatment spots on the skin in the direction of movement of the device, each pulse generating one of the treatment spots in the row and each treatment spot being spaced apart from each other treatment in the row by areas of non-treated skin.

25. A device for providing laser-based dermatological treatments, the device comprising:

a device body having an application end;

a VCSEL chip supported in the device body, the VCSEL chip including:

an array of micro-emitters formed integrally on a common substrate of a single monolithic chip, each micro-emitter configured to emit a micro-beam; and wherein the array of micro-emitters is divided into multiple emitter zones on the single chip, each emitter zone comprising one or more of the micro-emitters; and wherein at least two of the multiple emitter zones on the single monolithic chip have separate control interfaces configured such that the at least two emitter zones are independently controllable via the separate control interfaces;

a processor; and computer instructions stored in a non-transitory computer-readable medium and executable by the processor to independently control a current applied to each of the at least two of the emitter zones on the VCSEL chip via the separate control interfaces of the at least two of the multiple emitter zones.

26. The device of claim 25, wherein the multiple emitter zones on the single VCSEL chip are configured to generate multiple discrete treatment spots on the skin, the multiple discrete treatment spots being spaced apart from each other on the skin by areas of non-irradiated skin, with each emitter zone generating a single discrete treatment spot on the skin.

27. The device of claim 25, further comprising computer instructions executable to automatically pulse the micro-emitters provided on the VCSEL chip while the device is moved across the skin to generate a row of treatment spots on the skin in the direction of movement of the device, each pulse generating one of the treatment spots in the row and each treatment spot being spaced apart from each other treatment in the row by areas of non-treated skin.

28. The device of claim 1, wherein the computer instructions are executable to control the at least two emitter zones on the VCSEL chip independently by applying different currents to the at least two emitter zones to control a beam profile of the single combined beam collectively formed by the at least two emitter zones.

29. The method of claim 19, wherein executing the computer instructions to independently control the at least two emitter zones on the VCSEL chip comprises applying different currents to the at least two emitter zones to control a beam profile of the combined beam collectively formed by the at least two emitter zones.

* * * * *